(12) United States Patent  
Garvin et al.

(10) Patent No.: US 11,173,030 B2  
(45) Date of Patent: Nov. 16, 2021

(54) SUTURE LENGTH ADJUSTMENT FOR MINIMALLY INVASIVE HEART VALVE REPAIR

(71) Applicant: NeoChord, Inc., St. Louis Park, MN (US)

(72) Inventors: Graham Garvin, Redwood City, CA (US); Joel Helgerson, Boulder, CO (US); Tim Crowley, Arvada, CO (US); Tom Broome, Mound, MN (US); Daryl Edmiston, Draper, UT (US)

(73) Assignee: NeoChord, Inc., St. Louis Park, MN (US)

( * ) Notice: Subject to any disclaimer, the term of this patent is extended or adjusted under 35 U.S.C. 154(b) by 64 days.

(21) Appl. No.: 16/406,764

(22) Filed: May 8, 2019

(65) Prior Publication Data

US 2019/0343633 A1 Nov. 14, 2019

Related U.S. Application Data

(60) Provisional application No. 62/669,115, filed on May 9, 2018.

(51) Int. Cl.
*A61F 2/24* (2006.01)
*A61B 17/04* (2006.01)

(52) U.S. Cl.
CPC ........ *A61F 2/2457* (2013.01); *A61B 17/0401* (2013.01); *A61B 17/0487* (2013.01);
(Continued)

(58) Field of Classification Search
CPC .... A61B 2017/0403; A61B 2017/0496; A61B 2017/0404; A61B 2017/0464;
(Continued)

(56) References Cited

U.S. PATENT DOCUMENTS 2,751,908 A 6/1956 Wallace
3,664,330 A 5/1972 Deutsch
(Continued)

FOREIGN PATENT DOCUMENTS

EP 1039851 B1 7/2005
EP 1637091 A2 3/2006
(Continued)

OTHER PUBLICATIONS

Interactive Cardio Vascular and Thoracic Surgery; Abstracts; Suppl 3 to vol. 7 (Sep. 2008) 52 pages.
(Continued)

*Primary Examiner* — Dinah Baria
(74) *Attorney, Agent, or Firm* — Patterson Thuente Pedersen, P.A.

(57) ABSTRACT

Disclosed herein are various embodiments of suture adjustment mechanisms for anchors configured to be inserted into a heart wall of a patient to anchor a suture as an artificial chordae under an appropriate tension for proper valve function. Suture adjustment mechanisms can be configured to retain suture ends extending from the leaflet to the anchor with sufficient force to prevent natural movement of the leaflet from adjusting a length of the suture between the anchor and the leaflet. Free ends of the suture can extend from the anchor external to the body as tensioning strands. A surgeon can supply sufficient force on the tensioning strands from external the body to adjust a length and tension of the suture between the anchor and the leaflet.

22 Claims, 18 Drawing Sheets

(52) U.S. Cl.
CPC ............... *A61F 2220/0008* (2013.01); *A61F 2220/0091* (2013.01)

(58) Field of Classification Search
CPC .... A61B 2017/0417; A61B 2017/0419; A61B 17/0401; A61B 17/0487; A61F 2/2457; A61F 2220/0008; A61F 2220/0091
See application file for complete search history.

(56) References Cited

U.S. PATENT DOCUMENTS

| | | |
|---|---|---|
| 3,667,474 A | 6/1972 | Lapkin |
| 3,842,840 A | 10/1974 | Schweizer |
| 4,258,716 A | 3/1981 | Sutherland |
| 4,351,345 A | 9/1982 | Carney |
| 4,759,348 A | 7/1988 | Cawood |
| 4,836,204 A | 6/1989 | Landymore et al. |
| 4,935,027 A | 6/1990 | Yoon |
| 4,957,498 A | 9/1990 | Caspari et al. |
| 4,967,498 A | 9/1990 | Caspari |
| 4,960,424 A | 10/1990 | Grooters |
| 4,967,798 A | 11/1990 | Hammer |
| 4,972,874 A | 11/1990 | Jackson |
| 5,053,013 A | 10/1991 | Ensminger |
| 5,059,201 A | 10/1991 | Asnis |
| 5,211,650 A | 5/1993 | Noda |
| 5,297,536 A | 3/1994 | Wilk |
| 5,304,185 A | 4/1994 | Taylor |
| 5,312,423 A | 5/1994 | Rosenbluth et al. |
| 5,336,229 A | 8/1994 | Noda |
| 5,383,877 A | 1/1995 | Clarke |
| 5,431,666 A | 7/1995 | Sauer et al. |
| 5,452,733 A | 9/1995 | Sterman |
| 5,474,519 A | 12/1995 | Bloomer |
| 5,547,455 A | 8/1996 | McKenna et al. |
| 5,556,411 A | 9/1996 | Taoda et al. |
| 5,571,215 A | 11/1996 | Sterman |
| 5,601,578 A | 2/1997 | Murphy |
| 5,626,607 A | 5/1997 | Malecki |
| 5,653,716 A | 8/1997 | Malo et al. |
| 5,665,100 A | 9/1997 | Yoon |
| 5,667,472 A | 9/1997 | Finn et al. |
| 5,667,473 A | 9/1997 | Finn et al. |
| 5,667,478 A | 9/1997 | McFarlin et al. |
| 5,693,091 A | 12/1997 | Larson, Jr. et al. |
| 5,728,113 A | 3/1998 | Sherts |
| 5,762,458 A | 6/1998 | Wang et al. |
| 5,762,613 A | 6/1998 | Sutton et al. |
| 5,766,163 A | 6/1998 | Mueller et al. |
| 5,769,791 A | 6/1998 | Benaron et al. |
| 5,772,597 A | 6/1998 | Goldberger et al. |
| 5,772,672 A | 6/1998 | Toy et al. |
| 5,785,658 A | 7/1998 | Benaron et al. |
| 5,797,960 A | 8/1998 | Stevens et al. |
| 5,830,231 A | 11/1998 | Geiges, Jr. |
| 5,839,639 A | 11/1998 | Sauer et al. |
| 5,857,961 A | 1/1999 | Vanden Hoek et al. |
| 5,897,564 A | 4/1999 | Schulze et al. |
| 5,908,428 A | 6/1999 | Scirica et al. |
| 5,908,429 A | 6/1999 | Yoon |
| 5,919,128 A | 7/1999 | Fitch |
| 5,961,440 A | 10/1999 | Schweich, Jr. |
| 5,972,004 A | 10/1999 | Williamson et al. |
| 5,972,030 A | 10/1999 | Garrison et al. |
| 5,984,939 A | 11/1999 | Yoon |
| 5,993,466 A | 11/1999 | Yoon |
| 5,993,467 A | 11/1999 | Yoon |
| 6,022,360 A | 2/2000 | Reimels et al. |
| 6,045,497 A | 4/2000 | Schweich, Jr. |
| 6,050,936 A | 4/2000 | Schweich, Jr. |
| 6,053,933 A | 4/2000 | Balazs et al. |
| 6,059,715 A | 5/2000 | Schweich, Jr. |
| 6,077,214 A | 6/2000 | Mortier et al. |
| 6,117,144 A | 9/2000 | Nobles et al. |
| 6,129,683 A | 10/2000 | Sutton et al. |
| 6,149,660 A | 11/2000 | Laufer et al. |
| 6,152,934 A | 11/2000 | Harper et al. |
| 6,162,168 A | 12/2000 | Schweich, Jr. |
| 6,162,233 A | 12/2000 | Williamson |
| 6,165,119 A | 12/2000 | Schweich, Jr. |
| 6,165,120 A | 12/2000 | Schweich, Jr. |
| 6,165,183 A | 12/2000 | Kuehn et al. |
| 6,178,346 B1 | 1/2001 | Amundson et al. |
| 6,179,195 B1 | 1/2001 | Adams et al. |
| 6,183,411 B1 | 2/2001 | Mortier et al. |
| 6,190,357 B1 | 2/2001 | Ferrari et al. |
| 6,234,079 B1 | 5/2001 | Chertkow |
| 6,234,995 B1 | 5/2001 | Peacock, III |
| 6,245,079 B1 | 6/2001 | Nobles et al. |
| 6,260,552 B1 | 7/2001 | Mortier et al. |
| 6,261,222 B1 | 7/2001 | Schweich, Jr. |
| 6,264,602 B1 | 7/2001 | Mortier et al. |
| 6,269,819 B1 | 8/2001 | Oz et al. |
| 6,270,508 B1 | 8/2001 | KIleman et al. |
| 6,283,993 B1 | 9/2001 | Cosgrove et al. |
| 6,312,447 B1 | 11/2001 | Grimes |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,355,050 B1 | 3/2002 | Andreas et al. |
| 6,401,720 B1 | 6/2002 | Stevens et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,419,626 B1 | 7/2002 | Yoon |
| 6,436,107 B1 | 8/2002 | Wang et al. |
| 6,443,922 B1 | 9/2002 | Roberts et al. |
| 6,451,054 B1 | 9/2002 | Stevens |
| 6,461,366 B1 | 10/2002 | Seguin |
| 6,508,777 B1 | 1/2003 | Macoviak et al. |
| 6,514,194 B2 | 2/2003 | Schweich, Jr. et al. |
| 6,533,796 B1 | 3/2003 | Sauer et al. |
| 6,537,198 B1 | 3/2003 | Vidlund et al. |
| 6,537,314 B2 | 3/2003 | Langberg et al. |
| 6,551,331 B2 | 4/2003 | Nobles et al. |
| 6,558,416 B2 | 5/2003 | Cosgrove et al. |
| 6,562,052 B2 | 5/2003 | Nobles et al. |
| 6,564,805 B2 | 5/2003 | Garrison et al. |
| 6,582,388 B1 | 6/2003 | Coleman et al. |
| 6,585,727 B1 | 7/2003 | Cashman et al. |
| 6,589,160 B2 | 7/2003 | Schweich, Jr. et al. |
| 6,602,288 B1 | 8/2003 | Cosgrove et al. |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,629,984 B1 | 10/2003 | Chan |
| 6,645,205 B2 | 11/2003 | Ginn |
| 6,679,268 B2 | 1/2004 | Stevens et al. |
| 6,692,605 B2 | 2/2004 | Kerr et al. |
| 6,695,866 B1 | 2/2004 | Kuehn et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,733,509 B2 | 5/2004 | Nobles et al. |
| 6,740,107 B2 | 5/2004 | Loeb et al. |
| 6,743,239 B1 | 6/2004 | Kuehn et al. |
| 6,746,471 B2 | 6/2004 | Mortier et al. |
| 6,752,713 B2 | 6/2004 | Johnson, Jr. |
| 6,752,813 B2 | 6/2004 | Goldfarb et al. |
| 6,755,777 B2 | 6/2004 | Schweich, Jr. et al. |
| 6,764,510 B2 | 7/2004 | Vidlund et al. |
| 6,770,083 B2 | 8/2004 | Seguin |
| 6,770,084 B1 | 8/2004 | Bain et al. |
| 6,793,618 B2 | 9/2004 | Schweich, Jr. et al. |
| 6,802,860 B2 | 10/2004 | Cosgrove et al. |
| 6,808,488 B2 | 10/2004 | Mortier et al. |
| 6,810,882 B2 | 11/2004 | Langberg et al. |
| 6,840,246 B2 | 1/2005 | Downing |
| 6,858,003 B2 | 2/2005 | Evans et al. |

(56) References Cited

U.S. PATENT DOCUMENTS

| | | |
|---|---|---|
| 6,875,224 B2 | 4/2005 | Grimes |
| 6,893,448 B2 | 5/2005 | O'Quinn et al. |
| 6,896,686 B2 | 5/2005 | Weber |
| 6,908,424 B2 | 6/2005 | Mortier et al. |
| 6,918,917 B1 | 7/2005 | Nguyen et al. |
| 6,921,407 B2 | 7/2005 | Nguyen et al. |
| 6,929,715 B2 | 8/2005 | Fladda et al. |
| 6,936,054 B2 | 8/2005 | Chu |
| 6,955,175 B2 | 10/2005 | Stevens et al. |
| 6,962,605 B2 | 11/2005 | Cosgrove et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,991,635 B2 | 1/2006 | Takamoto et al. |
| 6,997,950 B2 | 2/2006 | Chawla |
| 7,004,176 B2 | 2/2006 | Lau |
| 7,004,952 B2 | 2/2006 | Nobles et al. |
| 7,011,669 B2 | 3/2006 | Kimblad |
| 7,044,905 B2 | 5/2006 | Vidlund et al. |
| 7,048,754 B2 | 5/2006 | Martin et al. |
| 7,077,862 B2 | 7/2006 | Vidlund et al. |
| 7,083,628 B2 | 8/2006 | Bachman |
| 7,083,638 B2 | 8/2006 | Foerster |
| 7,090,686 B2 | 8/2006 | Nobles et al. |
| 7,094,244 B2 | 8/2006 | Schreck |
| 7,100,614 B2 | 9/2006 | Stevens et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,118,583 B2 | 10/2006 | O'Quinn et al. |
| 7,122,040 B2 | 10/2006 | Hill et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,217,240 B2 | 5/2007 | Snow |
| 7,226,467 B2 | 6/2007 | Lucatero et al. |
| 7,247,134 B2 | 7/2007 | Vidlund et al. |
| 7,250,028 B2 | 7/2007 | Julian et al. |
| 7,288,097 B2 | 10/2007 | Seguin |
| 7,294,148 B2 | 11/2007 | McCarthy |
| 7,381,210 B2 | 6/2008 | Zarbatany et al. |
| 7,464,712 B2 | 12/2008 | Oz et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,386 B1 | 12/2009 | Gammie |
| 7,666,204 B2 | 2/2010 | Thornton et al. |
| 7,815,654 B2 | 10/2010 | Chu |
| 7,879,048 B2 | 2/2011 | Bain et al. |
| 7,887,552 B2 | 2/2011 | Bachman |
| 8,303,622 B2 | 11/2012 | Alkhatib |
| 8,465,500 B2 | 6/2013 | Speziali |
| 8,512,362 B2 | 8/2013 | Ewers et al. |
| 8,545,551 B2 | 10/2013 | Loulmet |
| 8,758,393 B2 | 6/2014 | Zentgraf |
| 8,771,296 B2 | 7/2014 | Nobles et al. |
| 8,938,283 B2 | 1/2015 | Zentgraf et al. |
| 8,968,338 B2 | 3/2015 | Speziali |
| 9,044,221 B2 | 6/2015 | Zentgraf et al. |
| 9,192,374 B2 | 11/2015 | Zentgraf |
| 9,364,213 B2 | 6/2016 | Speziali |
| 9,393,080 B2 | 7/2016 | Zentgraf et al. |
| 9,572,556 B2 | 2/2017 | Skinlo et al. |
| 9,668,860 B2 | 6/2017 | Kudlik et al. |
| 9,700,300 B2 | 7/2017 | Speziali |
| 9,877,833 B1 | 1/2018 | Bishop et al. |
| 10,080,659 B1 | 9/2018 | Zentgraf et al. |
| 10,130,474 B2 | 11/2018 | Zentgraf et al. |
| 10,213,306 B2 | 2/2019 | Colli |
| 10,314,586 B2 | 6/2019 | Greenberg et al. |
| 10,327,743 B2 | 6/2019 | St. Goar et al. |
| 10,499,941 B2 | 12/2019 | Suri |
| 10,507,018 B2 | 12/2019 | Zentgraf |
| 10,582,924 B2 | 3/2020 | Speziali |
| 10,588,620 B2 | 3/2020 | Caffes et al. |
| 10,695,178 B2 | 6/2020 | Zentgraf et al. |
| 10,765,715 B2 | 9/2020 | Kang et al. |
| 10,966,709 B2 | 4/2021 | Caffes et al. |
| 2001/0005787 A1 | 6/2001 | Oz |
| 2001/0016675 A1 | 8/2001 | Mortier et al. |
| 2001/0021872 A1 | 9/2001 | Bailey et al. |
| 2002/0013571 A1 | 1/2002 | Goldfarb et al. |
| 2002/0020732 A1 | 2/2002 | Adams et al. |
| 2002/0029080 A1 | 3/2002 | Mortier et al. |
| 2002/0049402 A1 | 4/2002 | Peacock, III |
| 2002/0077524 A1 | 6/2002 | Schweich, Jr. |
| 2002/0091382 A1 | 7/2002 | Hooven |
| 2002/0169359 A1 | 11/2002 | McCarthy |
| 2002/0173694 A1 | 11/2002 | Mortier et al. |
| 2002/0183766 A1 | 12/2002 | Seguin |
| 2002/0183787 A1 | 12/2002 | Wahr et al. |
| 2003/0004562 A1 | 1/2003 | DiCarlo |
| 2003/0032979 A1 | 2/2003 | Mortier et al. |
| 2003/0050529 A1 | 3/2003 | Vidlund et al. |
| 2003/0050693 A1 | 3/2003 | Quijano |
| 2003/0078599 A1 | 4/2003 | O'Quinn et al. |
| 2003/0078600 A1 | 4/2003 | O'Quinn et al. |
| 2003/0105519 A1 | 6/2003 | Fasol |
| 2003/0120341 A1 | 6/2003 | Shennib et al. |
| 2003/0130731 A1 | 7/2003 | Vidlund et al. |
| 2003/0163029 A1 | 8/2003 | Sonnenschein et al. |
| 2003/0166992 A1 | 9/2003 | Schweich, Jr. |
| 2003/0167071 A1 | 9/2003 | Martin et al. |
| 2003/0171641 A1 | 9/2003 | Schweich, Jr. |
| 2003/0181928 A1 | 9/2003 | Vidlund et al. |
| 2003/0187457 A1 | 10/2003 | Weber |
| 2003/0195529 A1 | 10/2003 | Takamoto et al. |
| 2003/0199975 A1 | 10/2003 | Gabbay |
| 2004/0003819 A1 | 1/2004 | St. Goar |
| 2004/0030382 A1 | 2/2004 | St. Goar |
| 2004/0039442 A1 | 2/2004 | St. Goar |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049552 A1 | 3/2004 | Motoyama |
| 2004/0087975 A1 | 5/2004 | Lucatero et al. |
| 2004/0087978 A1 | 5/2004 | Velez et al. |
| 2004/0092962 A1 | 5/2004 | Thornton et al. |
| 2004/0093023 A1 | 5/2004 | Allen et al. |
| 2004/0097805 A1 | 5/2004 | Verard et al. |
| 2004/0116767 A1 | 6/2004 | Lebovic |
| 2004/0122448 A1 | 6/2004 | Levine |
| 2004/0127983 A1 | 7/2004 | Mortier et al. |
| 2004/0133063 A1 | 7/2004 | McCarthy et al. |
| 2004/0167374 A1 | 8/2004 | Schweich et al. |
| 2004/0167539 A1 | 8/2004 | Kuehn et al. |
| 2004/0220593 A1 | 11/2004 | Grennhalgh |
| 2004/0225300 A1 | 11/2004 | Goldfarb et al. |
| 2004/0225304 A1 | 11/2004 | Vidlund et al. |
| 2004/0236353 A1 | 11/2004 | Bain et al. |
| 2004/0236354 A1 | 11/2004 | Seguin |
| 2004/0236373 A1 | 11/2004 | Anspach, III |
| 2004/0243229 A1 | 12/2004 | Vidlund et al. |
| 2004/0267083 A1 | 12/2004 | McCarthy |
| 2005/0004668 A1 | 1/2005 | Aklog et al. |
| 2005/0021055 A1 | 1/2005 | Toubia et al. |
| 2005/0021056 A1 | 1/2005 | St. Goar |
| 2005/0021057 A1 | 1/2005 | St. Goar |
| 2005/0033446 A1 | 2/2005 | Deem et al. |
| 2005/0044365 A1 | 2/2005 | Bachman |
| 2005/0065396 A1 | 3/2005 | Mortier et al. |
| 2005/0075723 A1 | 4/2005 | Schroeder et al. |
| 2005/0075727 A1 | 4/2005 | Wheatley |
| 2005/0101975 A1 | 5/2005 | Nguyen et al. |
| 2005/0125011 A1 | 6/2005 | Spence et al. |
| 2005/0131277 A1 | 6/2005 | Schweich, Jr. |
| 2005/0131533 A1 | 6/2005 | Alfieri et al. |
| 2005/0143620 A1 | 6/2005 | Mortier et al. |
| 2005/0148815 A1 | 7/2005 | Mortier et al. |
| 2005/0149014 A1 | 7/2005 | Hauck et al. |
| 2005/0154402 A1 | 7/2005 | Sauer et al. |
| 2005/0165419 A1 | 7/2005 | Sauer et al. |
| 2005/0171601 A1 | 8/2005 | Cosgrove |

(56) References Cited

U.S. PATENT DOCUMENTS

| | | |
|---|---|---|
| 2005/0216039 A1 | 9/2005 | Lederman |
| 2005/0240202 A1 | 10/2005 | Shennib et al. |
| 2005/0251187 A1 | 11/2005 | Beane et al. |
| 2006/0020275 A1 | 1/2006 | Goldfarb et al. |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0058871 A1 | 3/2006 | Zakay et al. |
| 2006/0074484 A1 | 4/2006 | Huber |
| 2006/0074485 A1 | 4/2006 | Realyvasquez |
| 2006/0089671 A1 | 4/2006 | Goldfarb et al. |
| 2006/0100699 A1 | 5/2006 | Vidlund et al. |
| 2006/0106305 A1 | 5/2006 | Lau |
| 2006/0127509 A1 | 6/2006 | Eckman |
| 2006/0135993 A1 | 6/2006 | Seguin |
| 2006/0149123 A1 | 7/2006 | Vidlund et al. |
| 2006/0161040 A1 | 7/2006 | McCarthy |
| 2006/0161193 A1 | 7/2006 | Beane et al. |
| 2006/0184203 A1 | 8/2006 | Martin et al. |
| 2006/0195012 A1 | 8/2006 | Mortier et al. |
| 2006/0195134 A1 | 8/2006 | Crittenden |
| 2006/0195183 A1 | 8/2006 | Navia et al. |
| 2006/0241340 A1 | 10/2006 | Vidlund |
| 2006/0287657 A1 | 12/2006 | Bachman |
| 2007/0002627 A1 | 1/2007 | Youn |
| 2007/0027451 A1 | 2/2007 | Desinger et al. |
| 2007/0038293 A1 | 2/2007 | St. Goar et al. |
| 2007/0049952 A1 | 3/2007 | Weiss |
| 2007/0050022 A1 | 3/2007 | Vidlund et al. |
| 2007/0055303 A1 | 3/2007 | Vidlund et al. |
| 2007/0088375 A1 | 4/2007 | Beane et al. |
| 2007/0100356 A1 | 5/2007 | Lucatero et al. |
| 2007/0112244 A1 | 5/2007 | McCarthy |
| 2007/0118151 A1 | 5/2007 | Davidson |
| 2007/0118154 A1 | 5/2007 | Crabtree |
| 2007/0118155 A1 | 5/2007 | Goldfarb et al. |
| 2007/0118213 A1 | 5/2007 | Loulmet |
| 2007/0129737 A1 | 6/2007 | Goldfarb et al. |
| 2007/0179511 A1 | 8/2007 | Paolitto |
| 2007/0197858 A1 | 8/2007 | Goldfarb et al. |
| 2007/0203391 A1 | 8/2007 | Bloom et al. |
| 2007/0232941 A1 | 10/2007 | Rabinovich |
| 2007/0239272 A1 | 10/2007 | Navia et al. |
| 2007/0265643 A1 | 11/2007 | Beane et al. |
| 2007/0299468 A1 | 12/2007 | Viola |
| 2008/0004485 A1 | 1/2008 | Moreschi |
| 2008/0027468 A1 | 1/2008 | Fenton, Jr. et al. |
| 2008/0051703 A1 | 2/2008 | Thornton et al. |
| 2008/0065011 A1 | 3/2008 | Marchand et al. |
| 2008/0065156 A1 | 3/2008 | Hauser et al. |
| 2008/0065205 A1 | 3/2008 | Nguyen et al. |
| 2008/0091059 A1 | 4/2008 | Machold |
| 2008/0091264 A1 | 4/2008 | Machold |
| 2008/0097482 A1 | 4/2008 | Bain et al. |
| 2008/0097489 A1 | 4/2008 | Goldfarb et al. |
| 2008/0109069 A1 | 5/2008 | Coleman et al. |
| 2008/0125860 A1 | 5/2008 | Webler |
| 2008/0125861 A1 | 5/2008 | Webler et al. |
| 2008/0167714 A1 | 7/2008 | St. Goar |
| 2008/0183194 A1 | 7/2008 | Goldfarb et al. |
| 2008/0188873 A1 | 8/2008 | Speziali |
| 2008/0195126 A1 | 8/2008 | Solem |
| 2008/0195200 A1 | 8/2008 | Vidlund et al. |
| 2008/0208006 A1 | 8/2008 | Farr |
| 2008/0228223 A1 | 9/2008 | Alkhatib |
| 2008/0243245 A1 | 10/2008 | Thamber et al. |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0125038 A1 | 5/2009 | Ewers et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. |
| 2009/0192598 A1 | 7/2009 | Lattouf et al. |
| 2009/0259304 A1 | 10/2009 | O'Beirne et al. |
| 2010/0030061 A1 | 2/2010 | Canfield et al. |
| 2010/0030242 A1 | 2/2010 | Nobles et al. |
| 2010/0042147 A1 | 2/2010 | Janovsky et al. |
| 2010/0121349 A1* | 5/2010 | Meier ............... A61B 17/0487 606/139 |
| 2010/0160726 A1 | 6/2010 | Windheuser |
| 2010/0174297 A1 | 7/2010 | Speziali |
| 2010/0185172 A1 | 7/2010 | Fabro |
| 2010/0217283 A1 | 8/2010 | St. Goar |
| 2010/0298929 A1 | 11/2010 | Thornton et al. |
| 2011/0011917 A1 | 1/2011 | Loulmet |
| 2012/0184971 A1 | 7/2012 | Zentgraf et al. |
| 2013/0035757 A1 | 2/2013 | Zentgraf et al. |
| 2013/0150710 A1 | 6/2013 | Zentgraf et al. |
| 2013/0158600 A1* | 6/2013 | Conklin ............ A61B 17/0483 606/232 |
| 2014/0031926 A1 | 1/2014 | Kudlik et al. |
| 2014/0039324 A1 | 2/2014 | Speziali |
| 2014/0364875 A1 | 12/2014 | Zentgraf |
| 2015/0148821 A1 | 5/2015 | Speziali |
| 2015/0190207 A1 | 7/2015 | Zentgraf et al. |
| 2015/0313620 A1 | 11/2015 | Suri |
| 2015/0313713 A1 | 11/2015 | Zentgraf et al. |
| 2015/0351741 A1* | 12/2015 | Hawkins ............ A61B 17/0401 606/232 |
| 2015/0351910 A1 | 12/2015 | Gilmore et al. |
| 2015/0366556 A1 | 12/2015 | Khairkhahan et al. |
| 2016/0106420 A1 | 4/2016 | Foerster et al. |
| 2016/0143737 A1 | 5/2016 | Zentgraf et al. |
| 2017/0245994 A1 | 8/2017 | Khairkhahan et al. |
| 2017/0290582 A1 | 10/2017 | Speziali |
| 2018/0161035 A1 | 6/2018 | Greenberg et al. |
| 2018/0280138 A1 | 10/2018 | Colli |
| 2018/0289483 A1 | 10/2018 | Kang et al. |
| 2019/0053902 A1 | 2/2019 | Zentgraf et al. |
| 2019/0133766 A1 | 5/2019 | Zentgraf et al. |
| 2019/0224012 A1 | 7/2019 | Colli |
| 2019/0290260 A1 | 9/2019 | Caffes et al. |
| 2019/0343626 A1 | 11/2019 | Smirnov et al. |
| 2019/0343634 A1 | 11/2019 | Garvin et al. |
| 2020/0093478 A1 | 3/2020 | Caffes et al. |
| 2020/0121314 A1 | 4/2020 | Speziali |
| 2020/0138430 A1 | 5/2020 | Zentgraf |
| 2020/0222186 A1 | 7/2020 | Edmiston et al. |
| 2020/0281582 A1 | 9/2020 | Caffes et al. |
| 2020/0330228 A1 | 10/2020 | Anderson et al. |
| 2020/0368022 A1 | 11/2020 | Zentgraf et al. |

FOREIGN PATENT DOCUMENTS

| | | |
|---|---|---|
| EP | 1845861 A2 | 10/2007 |
| EP | 1408850 B1 | 9/2009 |
| EP | 3441045 A1 | 2/2019 |
| JP | H 04307052 A | 10/1992 |
| JP | 06142114 | 5/1994 |
| JP | 2004-531337 A | 10/2004 |
| JP | 2007-535342 A | 12/2007 |
| WO | WO 1999/00059 A1 | 1/1999 |
| WO | WO 1999/30647 A1 | 6/1999 |
| WO | WO 2000/06026 A2 | 2/2000 |
| WO | WO 2000/06027 A2 | 2/2000 |
| WO | WO 2000/06028 A1 | 2/2000 |
| WO | WO 2000/16700 A1 | 3/2000 |
| WO | WO 2001/66018 A1 | 9/2001 |
| WO | WO 2001/95809 A1 | 12/2001 |
| WO | WO 2003/001893 A2 | 1/2003 |
| WO | WO 2003/059209 A2 | 7/2003 |
| WO | WO 2003/079937 A2 | 10/2003 |
| WO | WO 2003/082157 A2 | 10/2003 |
| WO | WO 2003/082158 A1 | 10/2003 |
| WO | WO 2004/021893 A1 | 3/2004 |
| WO | WO 2004/043265 A2 | 5/2004 |

(56) References Cited

FOREIGN PATENT DOCUMENTS

| | | |
|---|---|---|
| WO | WO 2005/039428 A2 | 5/2005 |
| WO | WO 2005/087140 A1 | 9/2005 |
| WO | WO 2005/094525 A2 | 10/2005 |
| WO | WO 2006/012750 A1 | 2/2006 |
| WO | WO 2006/032051 A2 | 3/2006 |
| WO | WO 2006/065966 A2 | 6/2006 |
| WO | WO 2006/078694 A2 | 7/2006 |
| WO | WO 2006/116310 A2 | 11/2006 |
| WO | WO 2006/127509 A2 | 11/2006 |
| WO | WO 2007/002627 A1 | 1/2007 |
| WO | WO 2007/027451 A2 | 3/2007 |
| WO | WO 2007/062128 A2 | 5/2007 |
| WO | WO 2007/081418 A1 | 7/2007 |
| WO | WO 2007/117612 A1 | 10/2007 |
| WO | WO 2008/010738 A2 | 1/2008 |
| WO | WO 2009/052528 A2 | 4/2009 |
| WO | WO 2011/070477 A1 | 6/2011 |
| WO | WO 2011/137336 A1 | 11/2011 |
| WO | WO 2012/167120 A2 | 12/2012 |
| WO | WO 2018/236766 A1 | 12/2018 |
| WO | WO 2019/183626 A1 | 9/2019 |
| WO | WO 2019/217638 A1 | 1/2020 |

OTHER PUBLICATIONS

Machine translation of JP 06142114.
Port Access System for Mitral Valve Repair Proves Its Value in Study; MedGadget Jul. 9, 2009 (2 pages).
Application and File History for U.S. Appl. No. 13/486,632, filed Jun. 1, 2012. Inventor Zentgraf et al.
Application and File History for U.S. Appl. No. 14/947,399, filed Nov. 20, 2015. Inventors: Zentgraf et al.
Application and File History for U.S. Appl. No. 16/406,736, filed May 8, 2019. Inventors: Smirnov et al.
Application and File History for U.S. Appl. No. 16/406,799, filed May 8, 2019. Inventors: Garvin et al.
Application and File History for U.S. Appl. No. 16/818,639, filed Mar. 13, 2020. Inventors: Caffes et al.
Application and File History for U.S. Appl. No. 16/363,701, filed Mar. 25, 2019. Inventors: Caffes et al.
Application and File History for U.S. Appl. No. 16/850,827, filed Apr. 16, 2020. Inventors: Anderson et al.
Application and File History for U.S. Appl. No. 16/564,887, filed Sep. 9, 2019. Inventors: Caffes et al.
Application and File History for U.S. Appl. No. 17/150,733, filed Jan. 15, 2021. Inventors: Edmiston et al.

\* cited by examiner

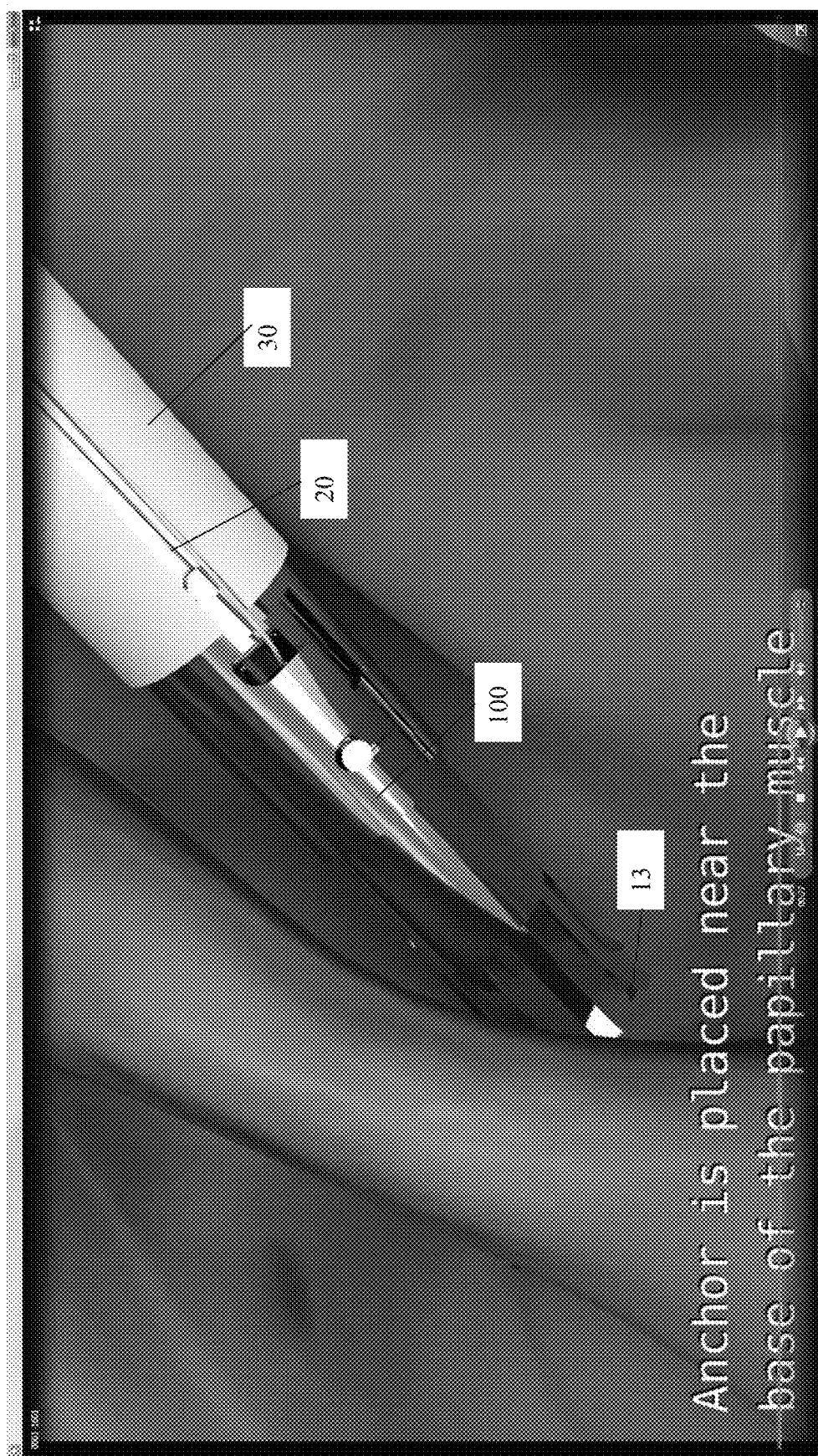

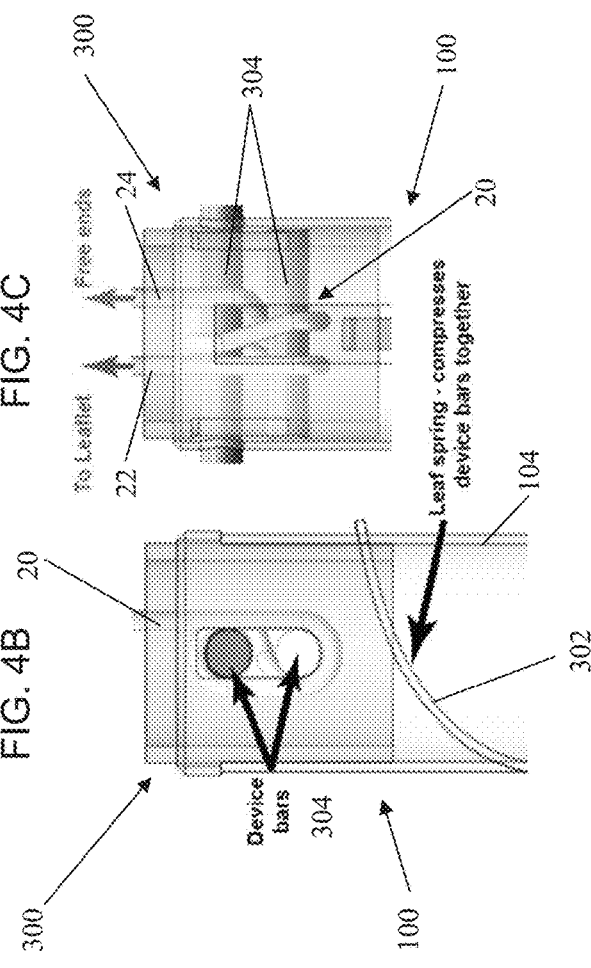
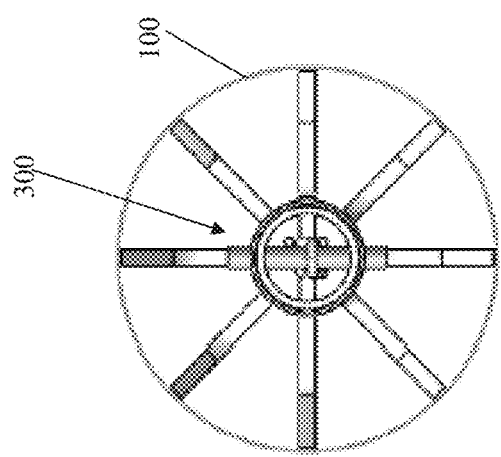

SUTURE LENGTH ADJUSTMENT FOR MINIMALLY INVASIVE HEART VALVE REPAIR

RELATED APPLICATION

This application claims the benefit of U.S. Provisional Application No. 62/669,115 filed May 9, 2018, which is hereby fully incorporated herein by reference.

TECHNICAL FIELD

The present invention relates to minimally invasive delivery of a suture. More particularly, the present invention relates to anchoring of a suture as an artificial chordae tendineae for a flailing or prolapsing leaflet in a beating heart.

BACKGROUND

The mitral and tricuspid valves inside the human heart include an orifice (annulus), two (for the mitral) or three (for the tricuspid) leaflets and a subvalvular apparatus. The subvalvular apparatus includes multiple chordae tendineae, which connect the mobile valve leaflets to muscular structures (papillary muscles) inside the ventricles. Rupture or elongation of the chordae tendineae results in partial or generalized leaflet prolapse, which causes mitral (or tricuspid) valve regurgitation. A commonly used technique to surgically correct mitral valve regurgitation is the implantation of artificial chordae (usually 4-0 or 5-0 Gore-Tex sutures) between the prolapsing segment of the valve and the papillary muscle.

This technique for implantation of artificial chordae was traditionally done by an open heart operation generally carried out through a median sternotomy and requiring cardiopulmonary bypass with aortic cross-clamp and cardioplegic arrest of the heart. Using such open heart techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of an artificial chordae through the atriotomy for attachment within the heart. However, these invasive open heart procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of such techniques.

Techniques for minimally invasive thoracoscopic repair of heart valves while the heart is still beating have also been developed. U.S. Pat. No. 8,465,500 to Speziali, which is incorporated by reference herein, discloses a thoracoscopic heart valve repair method and apparatus. Instead of requiring open heart surgery on a stopped heart, the thoracoscopic heart valve repair methods and apparatus taught by Speziali utilize fiber optic technology in conjunction with transesophageal echocardiography (TEE) as a visualization technique during a minimally invasive surgical procedure that can be utilized on a beating heart. More recent versions of these techniques are disclosed in U.S. Pat. Nos. 8,758,393 and 9,192,374 to Zentgraf, which disclose an integrated device that can enter the heart chamber, navigate to the leaflet, capture the leaflet, confirm proper capture, and deliver a suture as part of a mitral valve regurgitation (MR) repair. These minimally invasive repairs are generally performed through a small, between the ribs access point followed by a puncture into the ventricle through the apex of the heart. Although far less invasive and risky for the patient than an open heart procedure, these procedures still require significant recovery time and pain.

Some systems have therefore been proposed that utilize a catheter routed through the patient's vasculature to enter the heart and attach a suture to a heart valve leaflet as an artificial chordae. While generally less invasive than the approaches discussed above, transcatheter heart valve repair can provide additional challenges. For example, with all artificial chordae replacement procedures, in addition to inserting a suture through a leaflet, the suture must also be anchored at a second location, such as at a papillary muscle in the heart, with a suture length, tension and positioning of the suture that enables the valve to function naturally. If the suture is too short and/or has too much tension, the valve leaflets may not properly close. Conversely, if the suture is too long and/or does not have enough tension, the valve leaflets may still be subject to prolapse. Proper and secure anchoring of the suture away from the leaflet is therefore a critical aspect of any heart valve repair procedure for inserting an artificial chordae. However, adjusting length of a suture in a transcatheter procedure is difficult as it is not possible for the surgeon to physically control the suture and its length once the suture is in the heart.

SUMMARY

Disclosed herein are various embodiments of suture adjustment mechanisms for anchors configured to be inserted into a heart wall of a patient to anchor a suture as an artificial chordae under an appropriate tension for proper valve function. Suture adjustment mechanisms can be configured to retain suture ends extending from the leaflet to the anchor with sufficient force to prevent natural movement of the leaflet from adjusting a length of the suture between the anchor and the leaflet. Free ends of the suture can extend from the anchor external to the body as tensioning strands. A surgeon can supply sufficient force on the tensioning strands from external the body to adjust a length and tension of the suture between the anchor and the leaflet.

In one embodiment, a suture adjustment mechanism is embodied in an anchor configured to be implanted into a patient's heart wall to anchor a suture extending from a valve leaflet of the heart as an artificial chordae. The anchor can include an anchor body and a means for retaining a suture within the anchor body. The means for retaining a suture is configured to enable adjustment of a length of the suture extending between the anchor body and the valve leaflet by pulling tensioning strands of the suture extending from the anchor body out of the patient's heart while preventing forces applied on the length of the suture extending between the anchor body and the valve leaflet due to movement of the leaflet from adjusting the length of the suture extending between the anchor body and the valve leaflet.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 4A-4C depict a suture length and tension adjustment mechanism according to an embodiment.

Figure 1A:
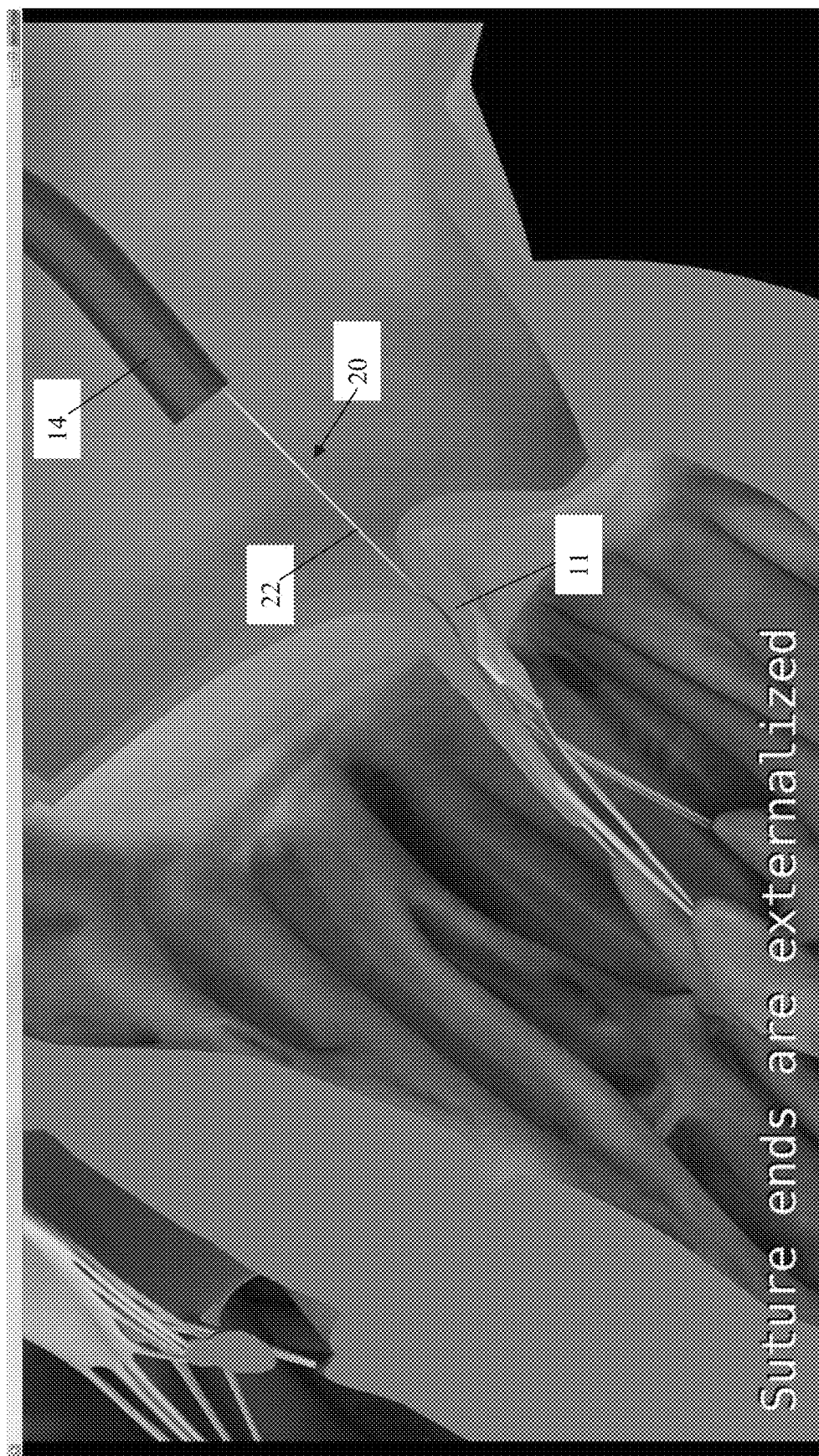
FIGS. 1A-1K depict various steps in a method of anchoring a suture in a beating heart of a patient to function as an artificial chordae according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The present disclosure is generally directed to adjusting a length and/or tension of sutures inserted as artificial chordae into one or more heart valve leaflets through an intravascular, transcatheter approach. A heart valve leaflet may be captured and a suture inserted through the leaflet in any manner known in the art. One such leaflet capture catheter and procedure is disclosed in copending U.S. Utility patent application Ser. No. 16/363,701, which is hereby incorporated by reference herein. Another transcatheter procedure for inserting an artificial chordae is disclosed in U.S. Patent Publication No. 2016/0143737, which is hereby incorporated by reference herein.

Referring to FIGS. 1A-1K, a procedure for anchoring a suture inserted as an artificial chordae in a transcatheter procedure on a beating heart of a patient following insertion of the suture into a leaflet is schematically depicted. In this embodiment, a loop of suture has been inserted through the leaflet and the two free ends of the suture then inserted through the loop to form a girth hitch knot around the edge of the leaflet. Further detail regarding attaching a suture to a leaflet in this manner can be found in U.S. Patent Publication No. 2017/0290582, which is hereby incorporated by reference herein.

Figure 1B:
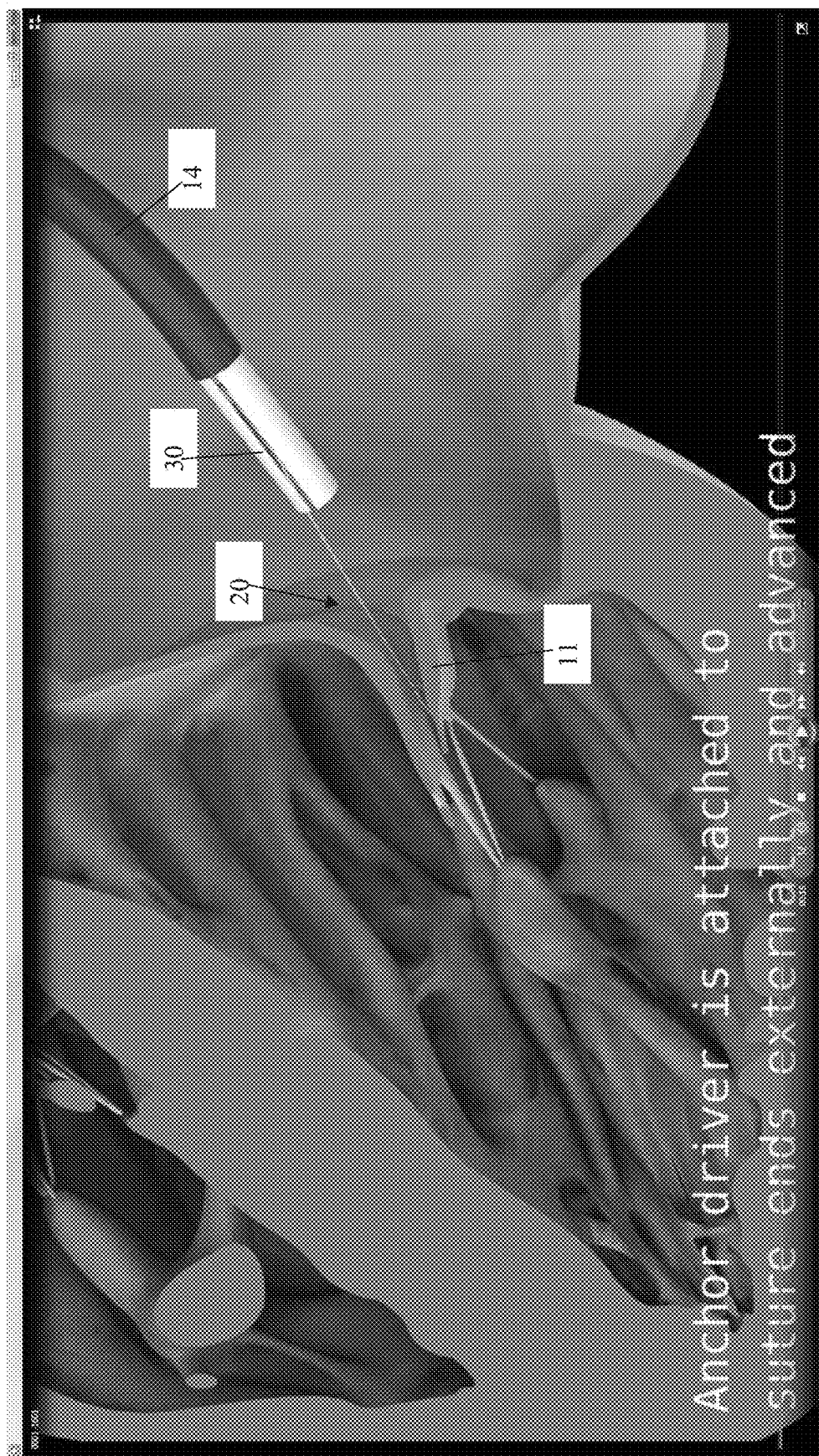
Figure 1C:
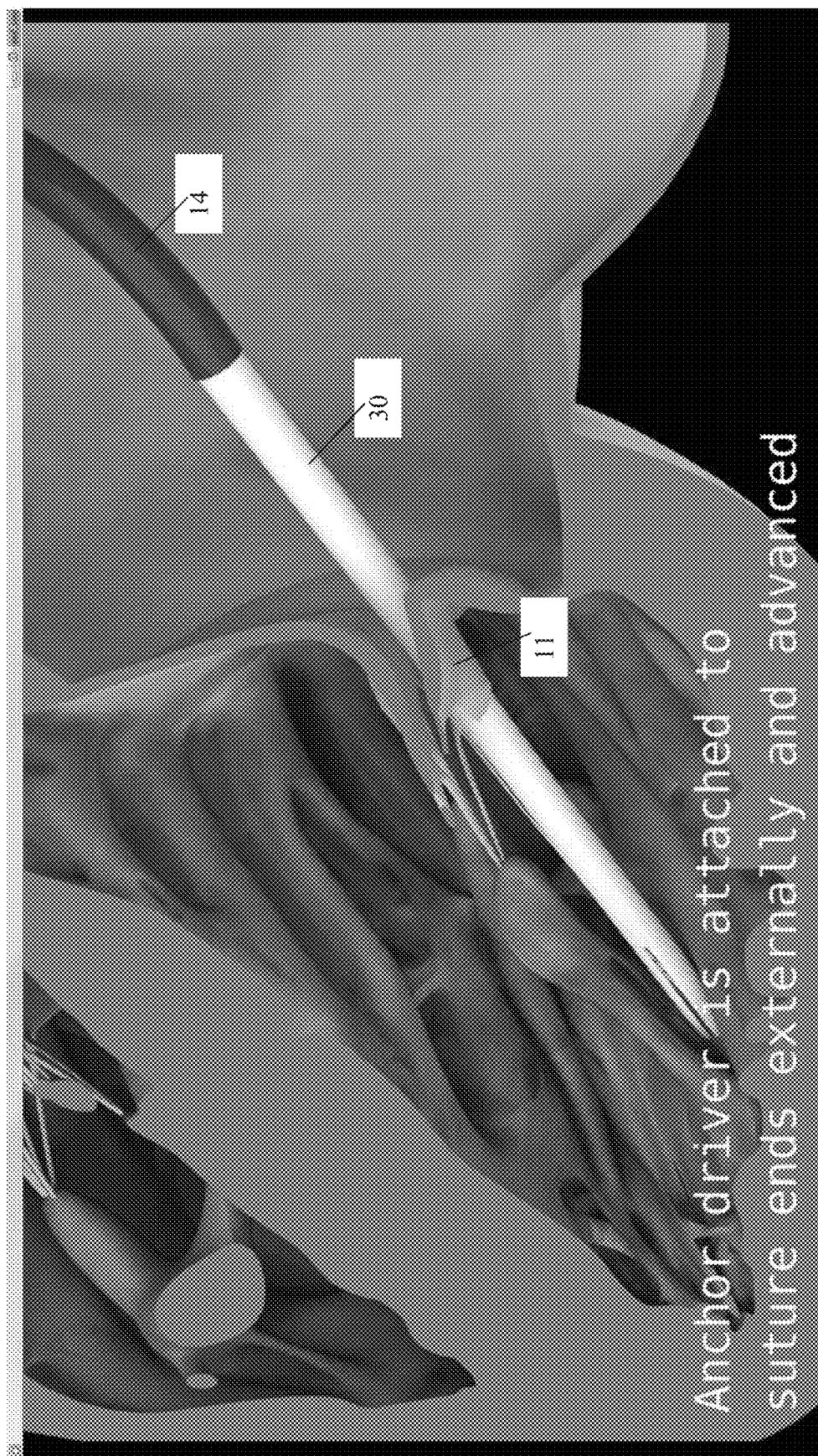
Figure 1D:
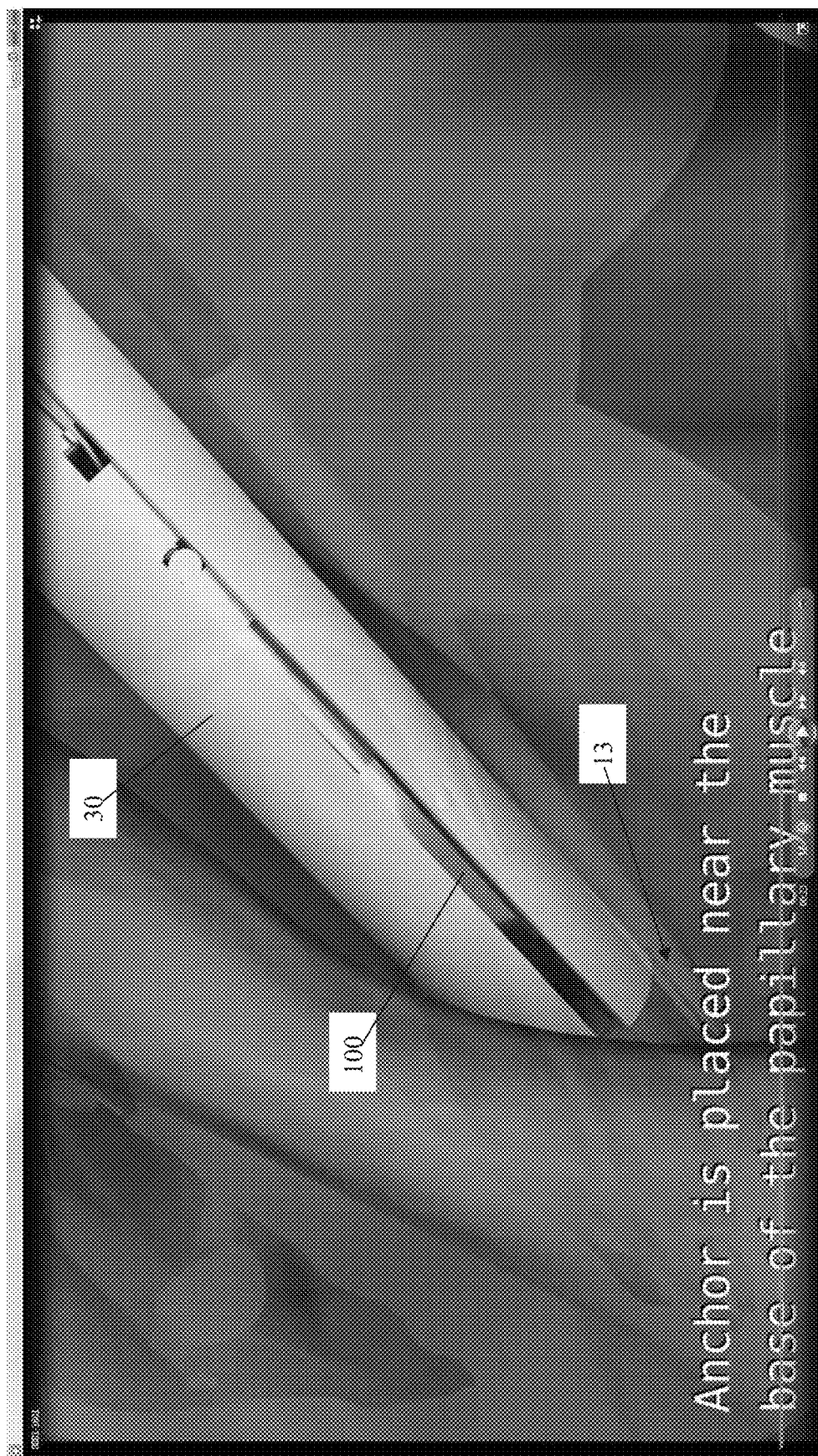
Figure 1E:
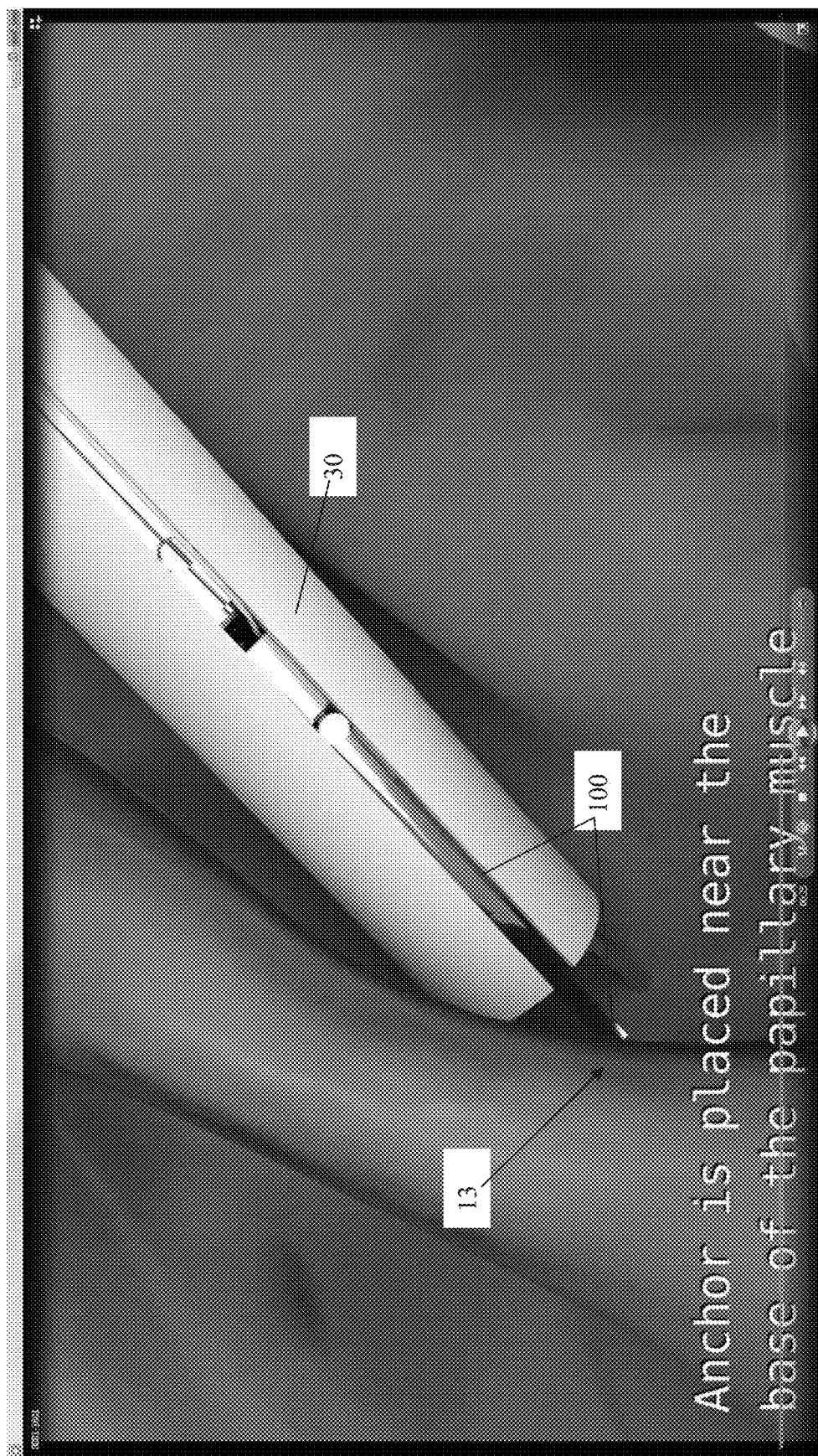
Figure 1G:
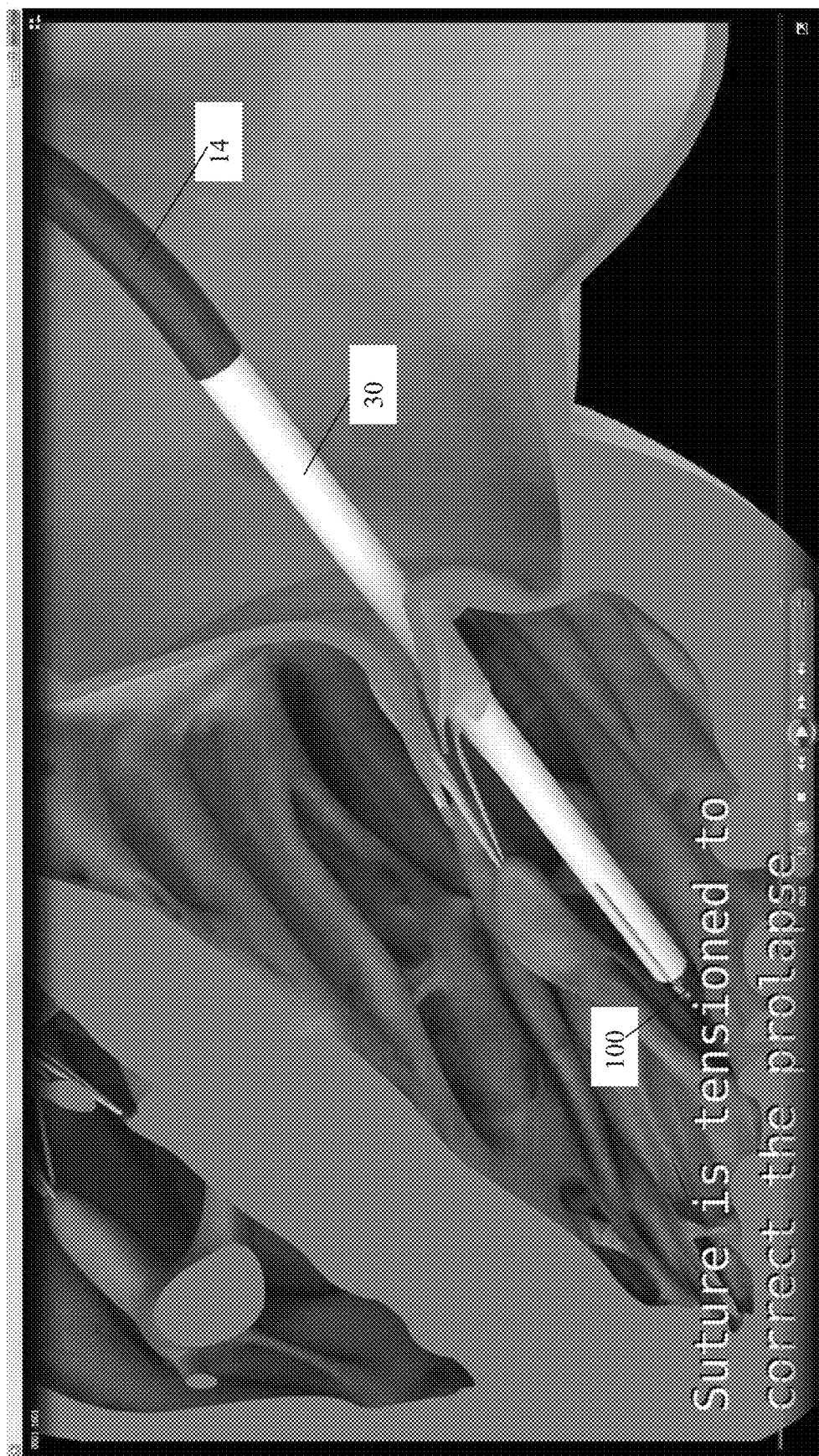

Following insertion of the suture 20 into the leaflet 11, the deployment catheter used to insert the suture is withdrawn through the guide catheter 14 and the two free ends 22 of the suture 20 are also withdrawn external to the body. The suture ends 22 are then attached to an anchor contained in an anchor driving catheter 30. Alternatively, the anchor could be pre-attached to the suture prior to insertion of the suture into the leaflet. The anchor driving catheter 30 is inserted into the guide catheter 14, routed through the catheter into the body and advanced passed the leaflet 11 to the heart wall 13 below the valve at, for example, a papillary muscle as shown in FIGS. 1B-1D. The anchor driving catheter 30 is then used to insert the anchor 100 into the myocardium as shown in FIGS. 1D-1G and as described in more detail below. Various embodiments of such anchors can be found in U.S. Provisional Patent Application Nos. 62/669,096 and 62/669,123, entitled Low Profile Tissue Anchor for Minimally Invasive Heart Valve Repair and Radial Arm Tissue Anchor for Minimally Invasive Heart Valve Repair, respectively, both of which are hereby incorporated by reference herein in their entireties.

Figure 1H:
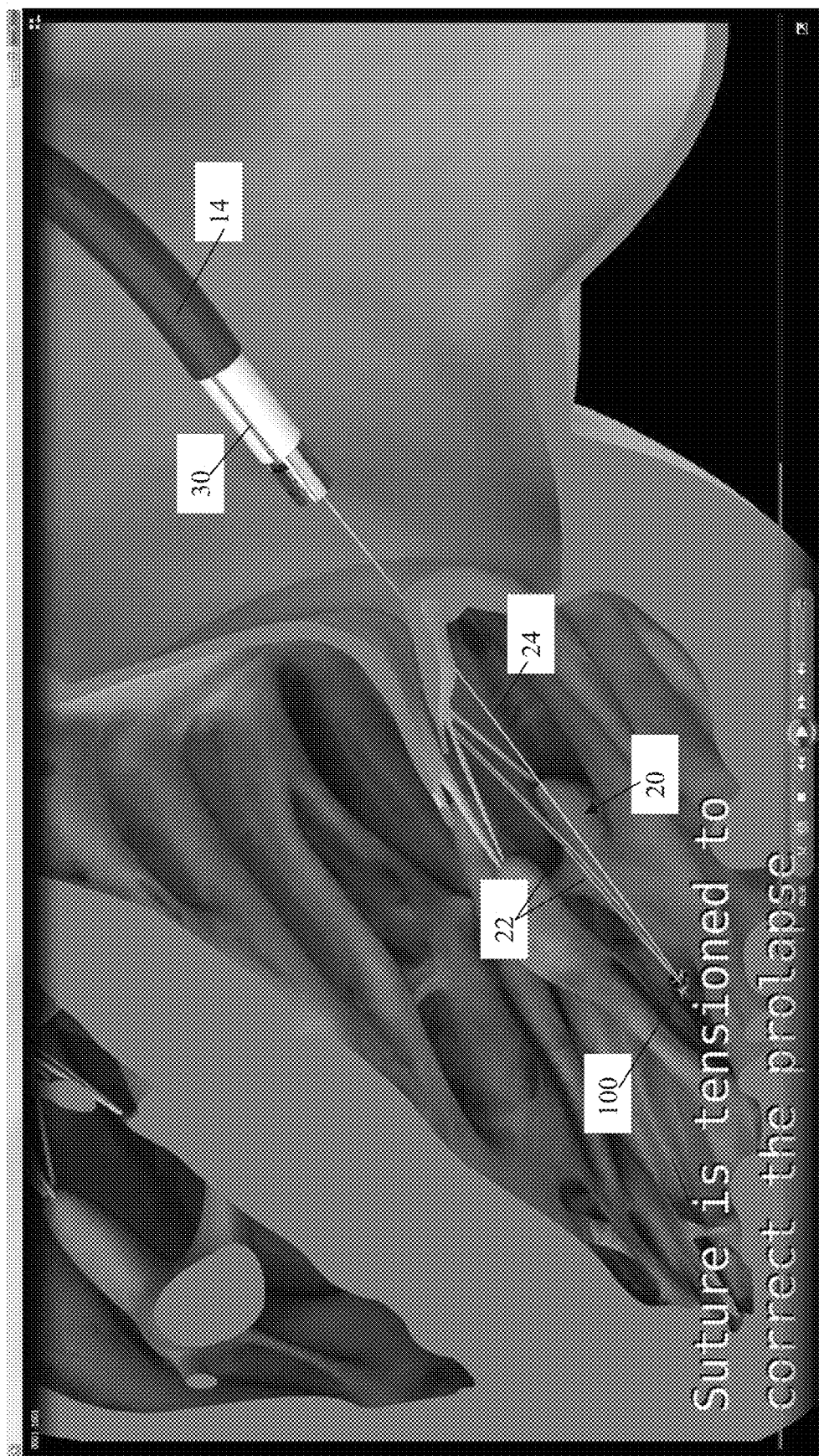
Figure 1:
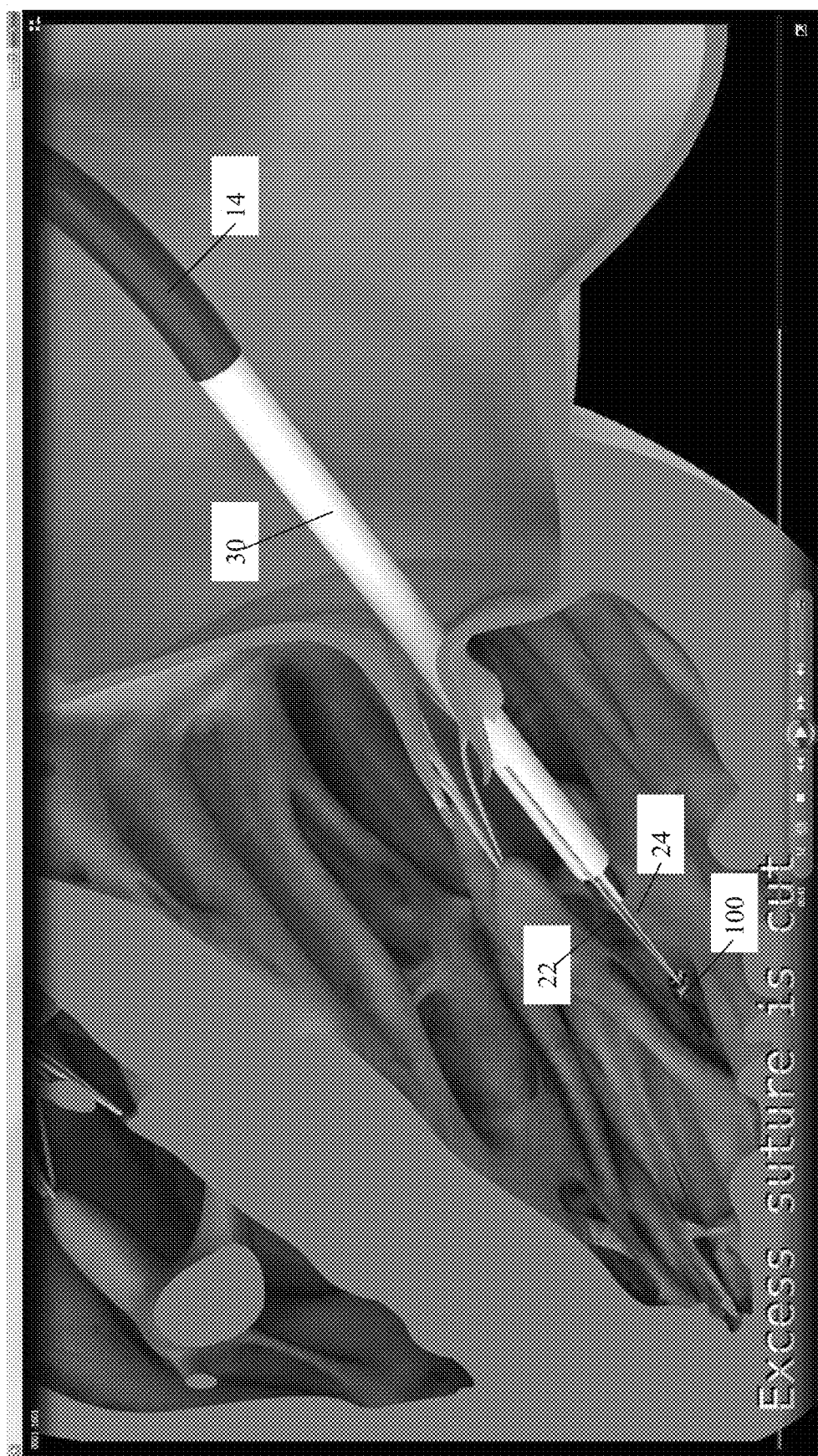
Figure 1J:
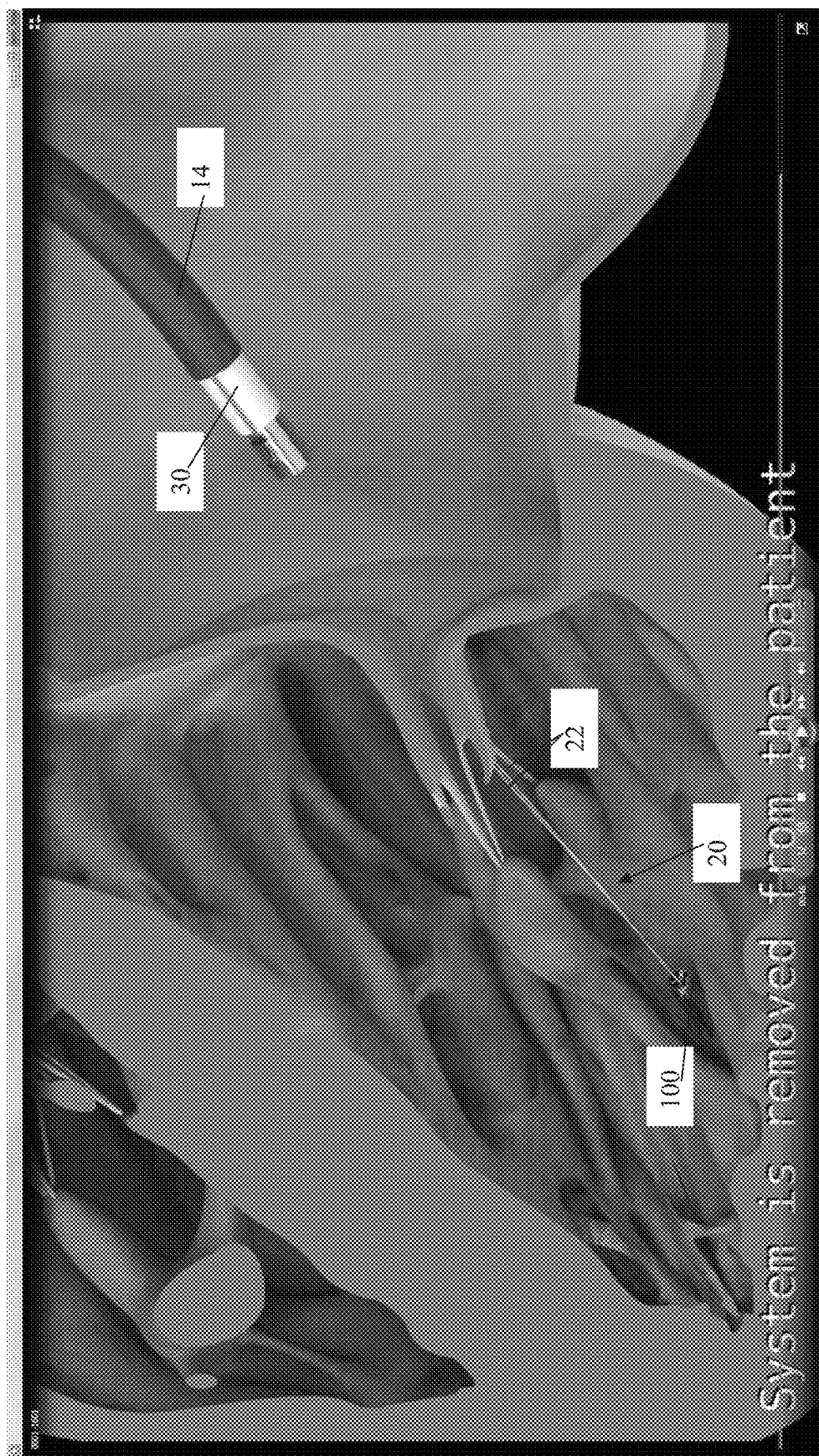
Figure 1K:
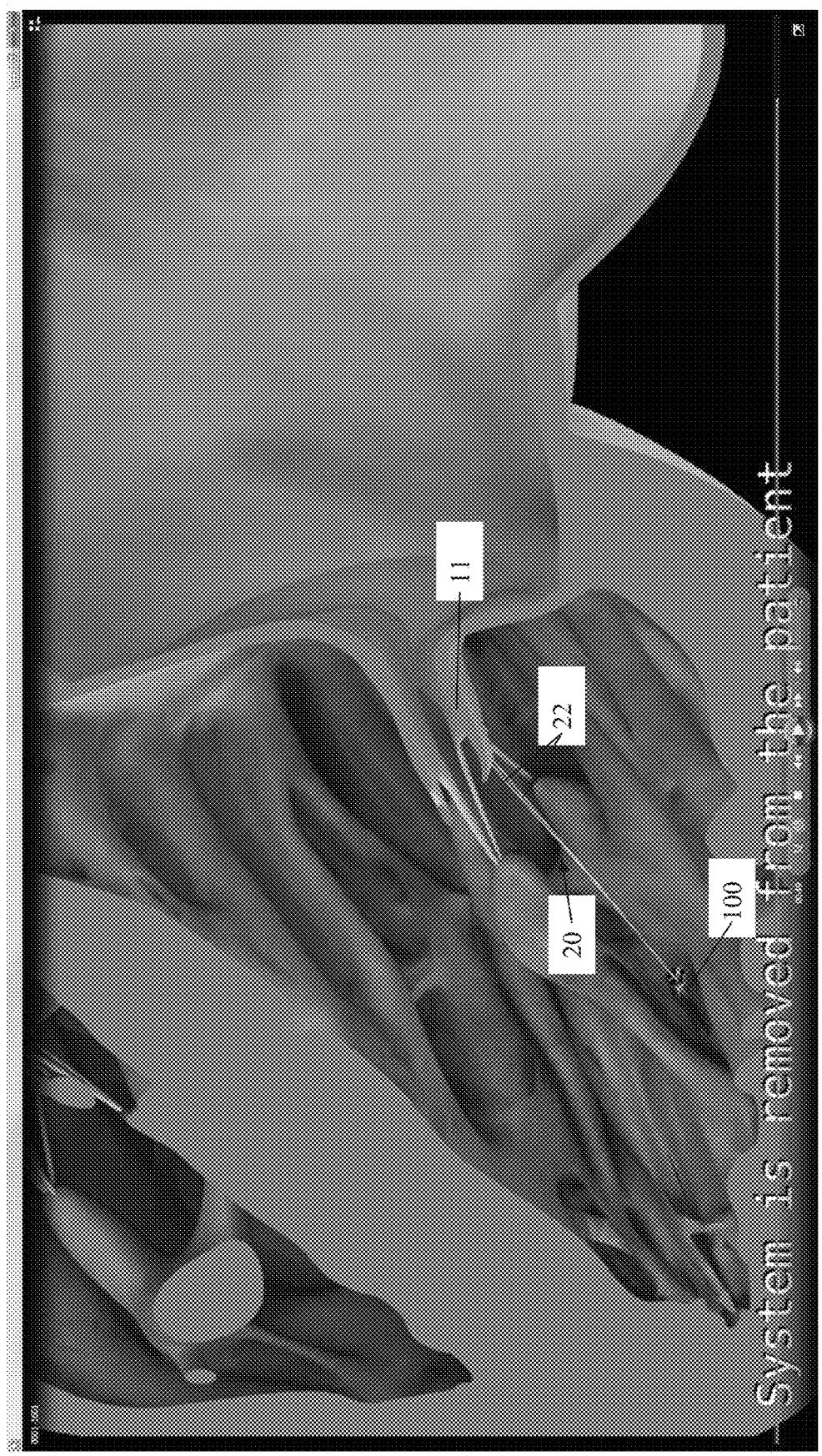

After insertion of the anchor 100 into the heart tissue, the anchor driving catheter 30 is withdrawn to a position superior of the valve as shown in FIG. 1H and the length and tension of the suture ends 22 extending from the leaflet 11 are tested and adjusted until it is determined that normal valve function has been achieved. This determination can be made through use of ultrasonic imaging, for example. The tension is adjusted through a tensioning strand 24 of the suture depicted in FIG. 1H. Once the proper length and tension has been determined using, for example, transesophageal echocardiography or other non-invasive methods, the anchor driving catheter 30 is advanced back down along the tensioning strand 24 and to sever the strand at the anchor 100, or a separate device configured to sever the strand can be used. The entire catheter system, including the anchor driving catheter 30 and the guide catheter 14 is then withdrawn from the patient's body. Referring to FIG. 1K, the suture 20 remains in the body extending between the leaflet 11 and the anchor 100 to function as an artificial chordae tendonae.

Figure 2A:
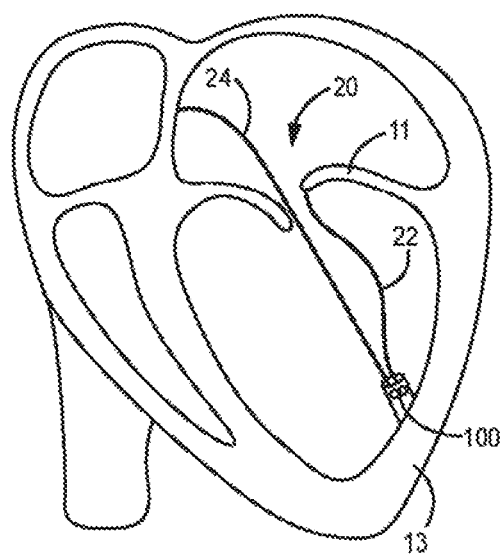
FIGS. 2A-2B depict steps in a method of anchoring a suture in a beating heart of a patient to function as an artificial chordae according to an embodiment.
Figure 2B:
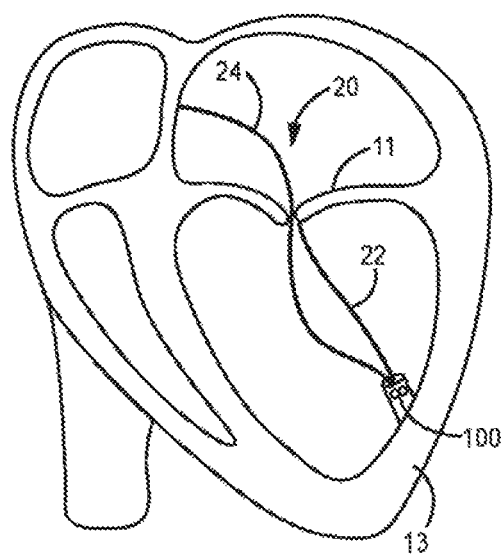

FIGS. 2A-2B depict further details regarding adjustment of the length and tension of the suture 20 according to an embodiment. After initial insertion of the anchor 100 into the heart wall 13, the free ends 22 of the suture 20 extend between the anchor and the leaflet 11 and the tensioning strand 24 of the suture 20 extends out of the body where it is accessible to the surgeon, as described above. FIG. 2A depicts one example of an initial configuration prior to suture adjustment. In the depicted configuration, a length of the suture ends 22 between the anchor 100 and the leaflet 11 is too long such that there is not enough tension on the leaflet 11, which could cause the leaflet 11 to continue to prolapse. FIG. 2B depicts a final configuration after suture adjustment. In this configuration, the length of the suture ends 22 between the anchor 100 and the leaflet 11 have been shortened to provide a tension that enables the leaflet 11 to coapt with the other leaflet during systole while preventing the leaflet 11 from prolapsing. Once proper suture length and tension has been achieved as shown in FIG. 2B, the tensioning strand 24 can be severed as discussed above.

Disclosed herein are various embodiments of mechanisms that can be employed to adjust the length and/or tension of a suture as an artificial chordae in procedures such as those described above. Such mechanisms enable suture adjustment from outside the body in a transcatheter, intravascular procedure.

FIGS. 3A-3E depict a suture adjustment mechanism 200 of a suture anchor 100 according to an embodiment. Suture adjustment mechanism 200 can be disposed adjacent a proximal portion of an anchor body 104 of suture anchor 100. For sake of clarity, only body portion 104 of suture anchor 100 is depicted. Although not shown in these figures for sake of clarity, suture anchor 100 would further include a distal portion for embedding the anchor into heart tissue, such as, for example those disclosed in the toggle anchor and spider anchor applications incorporated by references above.

Suture adjustment mechanism 200 includes an actuation tube 202 and a pair of pins or bars 204. Actuation tube 202 can surround a portion of anchor body 104 of anchor 100. Bars 204 can extend transversely across a long axis of anchor body 104. Bars 204 can extend through and be supported within opposing apertures 105 through anchor body 104. Bars 204 can further extend through and be supported within opposing apertures 205 in the actuation tube 202 adjacent the apertures 105 in the anchor body 104. In the depicted embodiment, bars 204 can seat within apertures 105, 205, in a generally horizontal side-by-side and parallel configuration with each other. An actuation projection 206 on one or both sides of the actuation tube can extend from actuation tube 202 into the aperture 205 and can be selectively positioned between pins, as will be discussed below.

Figure 3B:
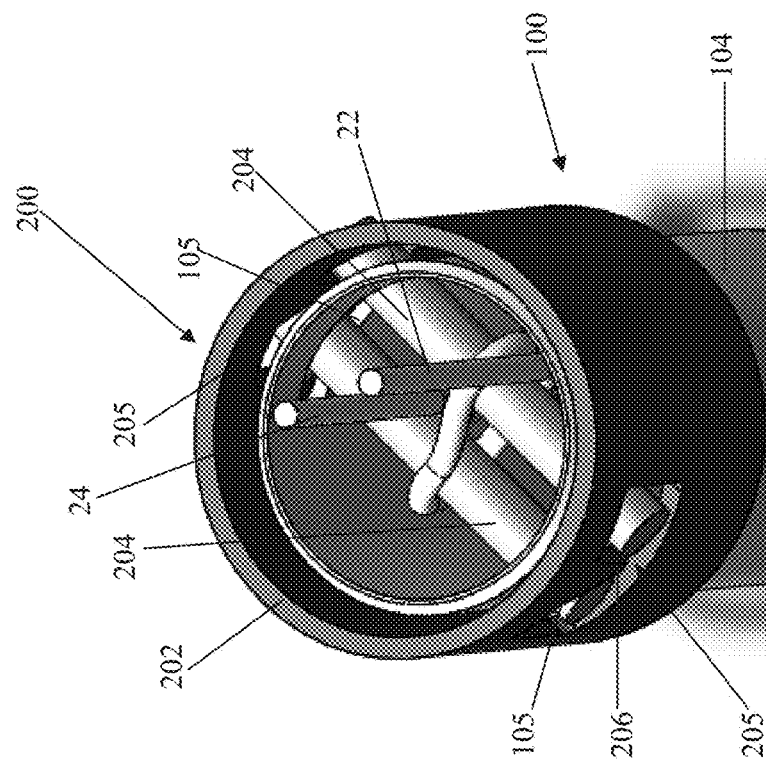
FIGS. 3A-3F depict a suture length and tension adjustment mechanism according to an embodiment.
Figure 3A:
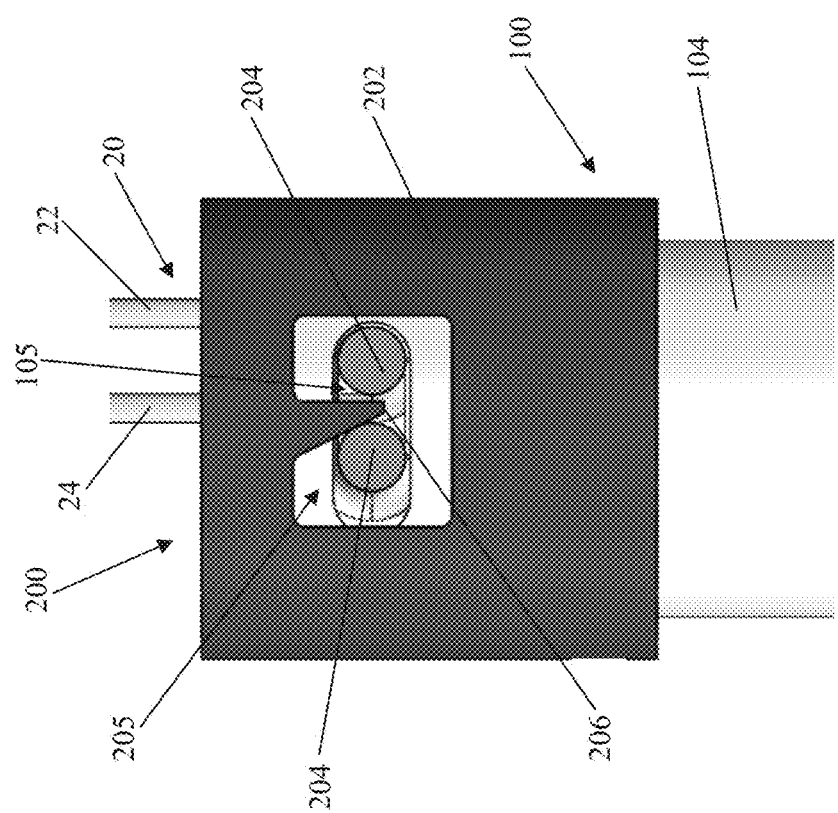
Figure 3C:
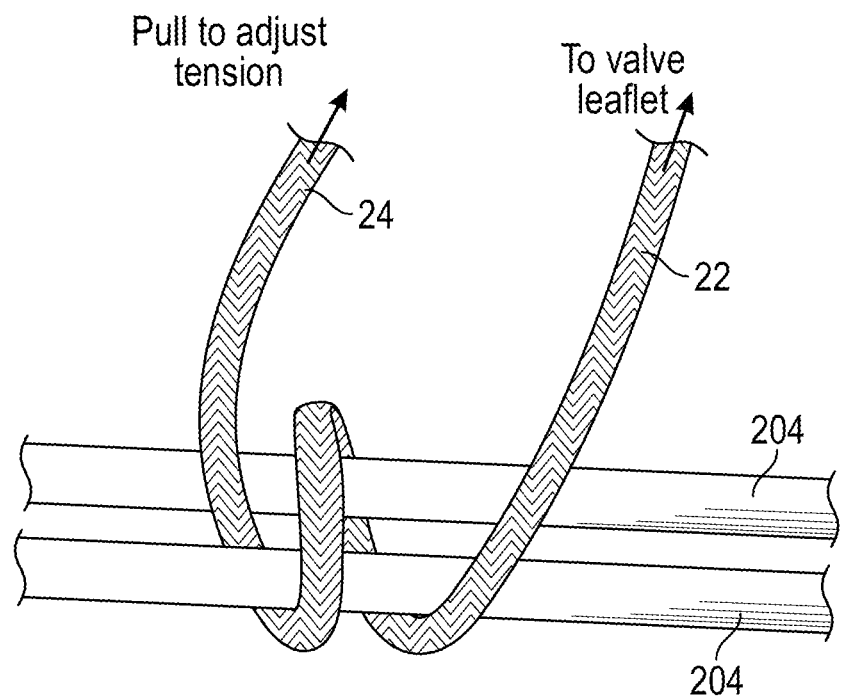
Figure 3D:
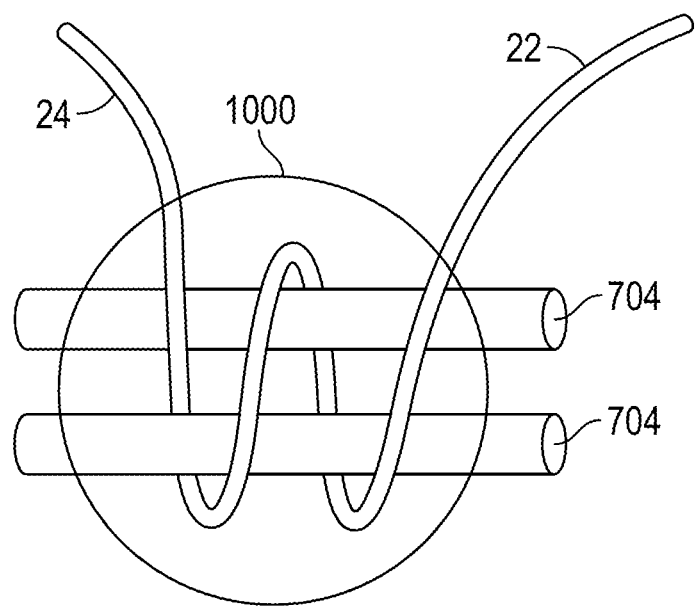

A suture 20 can extend into anchor body 104 and be wrapped around pins/bars as shown in more detail in FIGS. 3B-3D. For sake of clarity, it is noted that only a single suture end is shown in these Figures. However, it should be noted that each suture inserted through a leaflet will have a pair of suture ends attached to the suture adjustment mechanism 200. As shown in these figures, each suture end 22 extending from the leaflet to the anchor 100 wraps completely around both pins/bars. The suture 20 then extends between the bars 204 as tensioning strands 24 extending back out of the body to the surgeon, as described above.

Figure 3F:
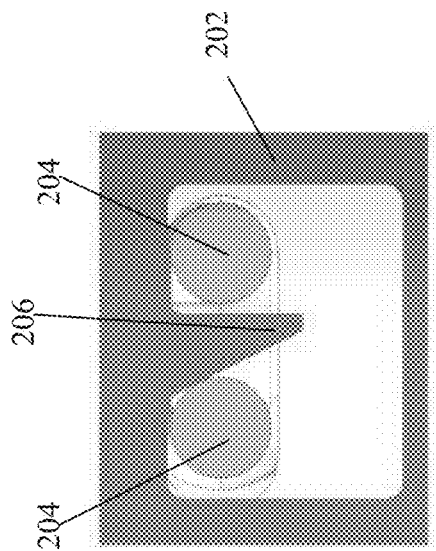
Figure 3E:
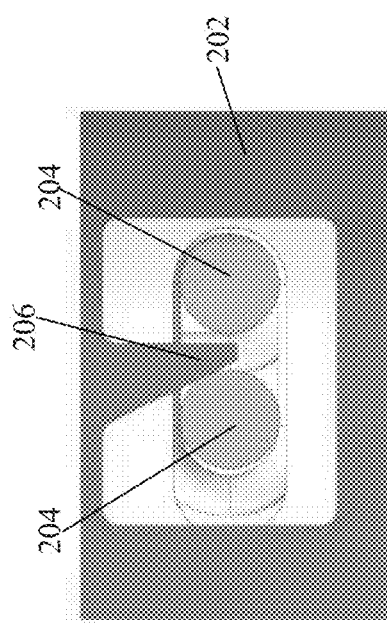

The actuation projection 206 of actuation tube 202 can be biased to a proximal position as shown in FIG. 3E and can be actuated downwardly as shown in FIG. 3F to drive the bars 204 apart. In use, when anchor 100 is attached to the anchor delivery catheter 30, the delivery catheter 30 can interface with the actuation tube 202 to actuate the projection 206 downwardly to force the bars 204 apart. This space between the bars 204 enables the anchor 100 to slide along the tensioning strand 24 from a position outside the body where the anchor 100 is attached to the suture 20 to within the heart adjacent the myocardium where the anchor 100 is to be inserted. Following insertion of the anchor 100, the anchor delivery catheter 30 is withdrawn as discussed above. Once the anchor delivery catheter 30 is detached from the actuation tube 202, the tube returns to the proximal position shown in FIG. 3E and the tensioning strand 24 of the suture 20 is held between the bars 204 with sufficient force such that the forces applied to the free ends 22 of the suture (wrapped around the bars 204) by the natural movement of the leaflet to which the suture is attached are not sufficient to move the suture. However, a surgeon operating the tensioning strands 24 of the suture 20 external to the body can supply sufficient force by pulling on the tensioning strands 24 to shorten the distance between the anchor 100 and the leaflet (see FIGS. 2A-2B). The actuation tube can be utilized to release the suture tension applied to the valve leaflet in a situation where increasing the length of the suture between the anchor and the leaflet is desired by the surgeon following the assessment of the valve function. Once the tension and length of the suture 20 have been properly adjusted and the tensioning strand 24 is severed as discussed above, the suture length will be fixed.

FIGS. 4A-4C depict a suture adjustment mechanism 300 according to another embodiment. Suture adjustment mechanism 300 is similar to suture adjustment mechanism 200 in that the suture 20 wraps around a pair of bars or pins 304 contained in a proximal portion of an anchor body 104 of suture anchor 100. In contrast to the generally horizontally aligned bars 204 of suture adjustment mechanism 200, the bars 304 of suture adjustment mechanism 300 are oriented and aligned generally vertically with respect to each other. Bars 304 can extend through the anchor body 104 similar to the embodiment described above.

The suture ends 22 extending between the leaflet and the anchor 100 wrap around the bars 304 and the free ends or tensioning strands 24 extend between the bars 304, as shown in FIGS. 4B-4C. A leaf spring 302 can be positioned within anchor body 104 to apply a force to bias the bars together, either by directly contacting the lower bar 304 or by contact a housing element that contains the pins. Tension on the suture and the length between the anchor 100 and the leaflet can be adjusted by pulling on the tensioning strands 24 outside the body with sufficient force to pull the suture 20 through the bars 204 and shorten the connection to the leaflet. In one embodiment, the force required by the surgeon to pull the suture through the mechanism is 0.1 pounds. Natural forces of the leaflet on the suture ends 22 are not sufficient to pull the suture through the bars 304, and because the suture ends 22 are wrapped around the pins 304 such forces increase the inward clamping force provided by bars 304 to the tensioning strands 24 positioned therebetween. Tension can be released by exerting force downward onto leaf spring to enable the pins to spread apart. Such a force can be applied by, for example, a catheter such as delivery catheter 30 as the anchor 100 is advanced from external the body along the suture 20 to the myocardium where it is to be anchored.

Figure 5:
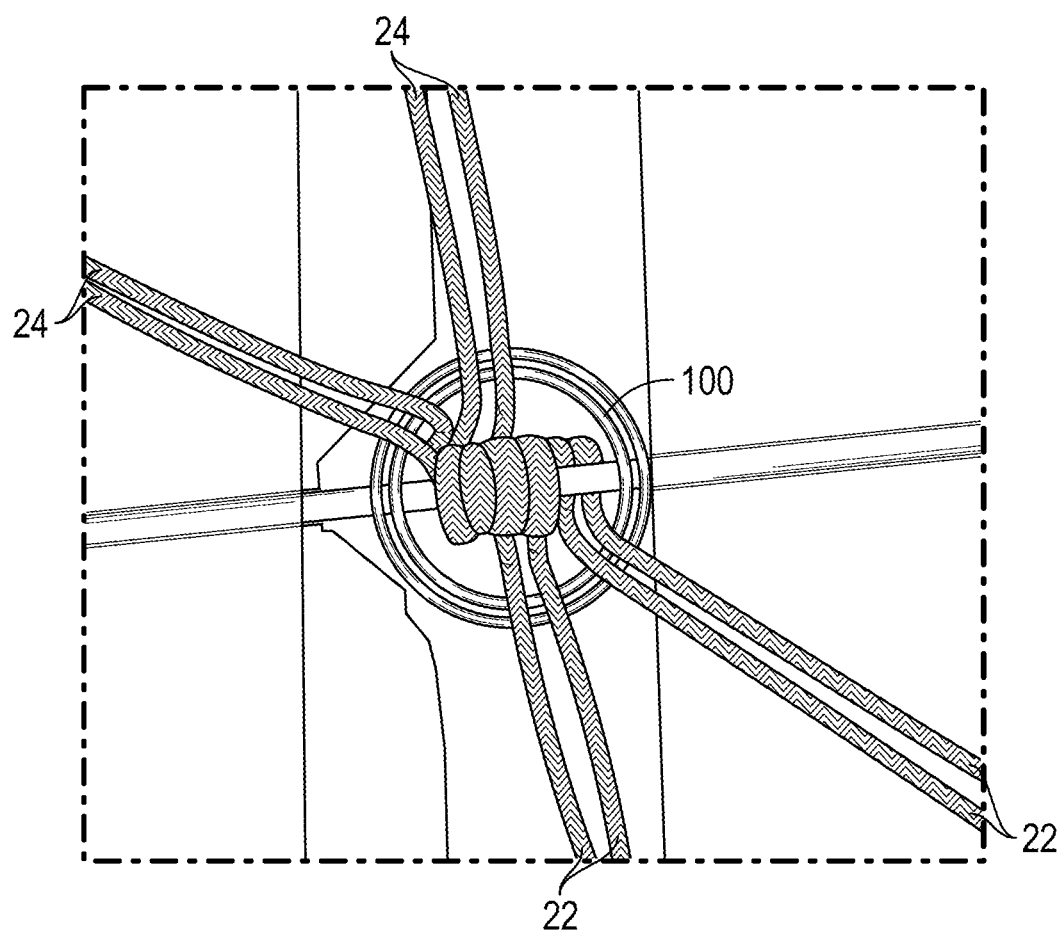
FIG. 5 depicts a suture length and tension adjustment mechanism according to an embodiment.

As noted above, in the previous embodiments only a single suture end has been shown for sake of clarity. In practice, each suture will have a pair of ends 22 extending from the leaflet and a corresponding pair of tensioning strands 24. In one embodiment, each anchor 100 and corresponding tensioning mechanism 200, 300 can accommodate a pair of sutures connected to the leaflet, which therefore includes two pairs (4) of suture ends 22 extending to the leaflet and two pairs (4) of tensioning strands 24 extending out of the body, as depicted schematically in FIG. 5.

Figure 6B:
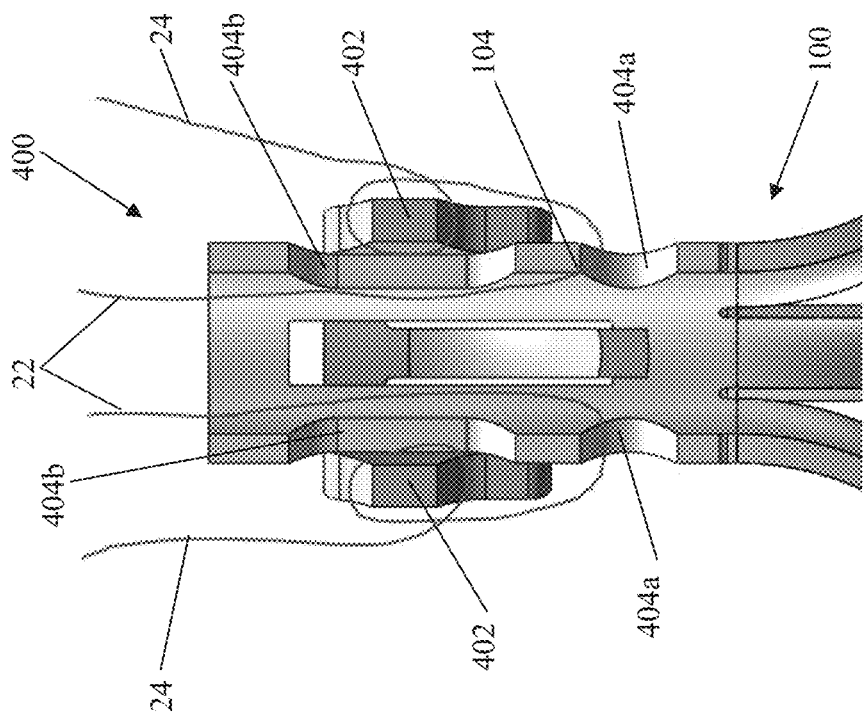
FIGS. 6A-6B depict a suture length and tension adjustment mechanism according to an embodiment.
Figure 6A:
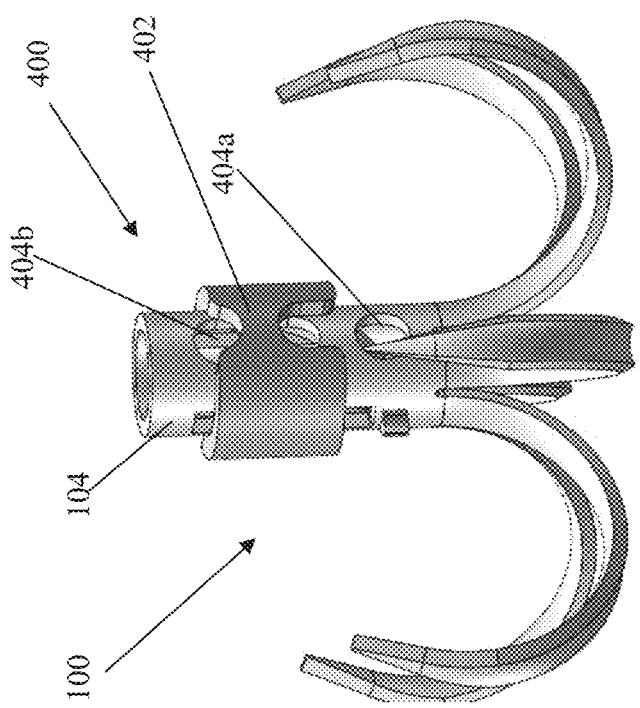

FIGS. 6A-6B depict a suture adjustment mechanism 400 defined in an anchor body 104 of an anchor 100 according to a further embodiment. Essentially, this embodiment replaces the pins or bars 204, 304 of the previous embodiments with apertures 404 formed through opposing sides of the anchor body 104. In one embodiment, apertures 404 include a distal aperture 404a and a proximal aperture 404b. In the depicted embodiment, the distal apertures 404a are generally circular and the proximal apertures 404b are elongate. Suture adjustment mechanism 400 can further include a suture wrapping sleeve 402. Suture wrapping sleeve 402 can be positioned around the elongate proximal apertures 404b.

Referring to FIG. 6B, each suture end 22 of a suture 20 extending from the leaflet enters into anchor body 104 through an open proximal end of anchor body 104 and extends into a hollow interior of anchor body 104. The suture ends 22 then extend out of the distal apertures 404a and are wrapped around the suture wrapping sleeve 402 at the elongate proximal apertures 404b. The suture 20 then extends back out of the body as a pair of tensioning strands 24 for adjusting a length of each respective suture end 22 relative to the leaflet. As with previous embodiments, a surgeon can provide sufficient force on the tensioning strands 24 to adjust the length and tension of the suture ends 22, but the natural forces of the leaflet are insufficient to adjust the wrapped suture ends 22.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. An anchor configured to be implanted into a heart wall of a heart of a patient to anchor a suture extending from a valve leaflet of the heart as an artificial chordae, the anchor comprising:
    an anchor body; and
    means for retaining a suture within the anchor body, wherein the means for retaining the suture is configured to enable adjustment of a length of the suture extending between the anchor body and the valve leaflet by pulling tensioning strands of the suture extending from the anchor body out of the heart while preventing forces applied on the length of the suture extending between the anchor body and the valve leaflet due to movement of the leaflet from adjusting the length of the suture extending between the anchor body and the valve leaflet, wherein the means for retaining a suture within the anchor body is a pair of pins disposed within the anchor body, the pair of pins comprising a first bar extending across a width of the anchor body and a second bar extending across the width of the anchor body with the first bar and the second bar being separate structures from each other and the anchor body.

2. The anchor of claim 1, wherein the pair of pins are oriented in a generally horizontal configuration with respect to each other.

3. The anchor of claim 1, wherein the pair of pins are oriented in a generally vertical configuration with respect to each other.

4. The anchor of claim 1, further comprising means for adjusting a clamping force by which the pins retain the suture.

5. The anchor of claim 4, wherein the means for adjusting a clamping force comprises a leaf spring that biases the pins into a compressed configuration to retain the suture by a clamping force between the pins.

6. The anchor of claim 5, wherein the leaf spring is configured to be engaged to separate the pins to lessen the clamping force on the suture.

7. The anchor of claim 4, wherein the means for adjusting a clamping force comprises a sleeve extending around the anchor body.

8. The anchor of claim 7, wherein the sleeve is configured to be actuated to separate the pins to lessen the clamping force on the suture.

9. An anchor configured to be implanted into a heart wall of a heart of a patient to anchor a suture extending from a valve leaflet of the heart as an artificial chordae, the anchor comprising:
    an anchor body; and
    means for retaining a suture within the anchor body, wherein the means for retaining the suture is configured to enable adjustment of a length of the suture extending between the anchor body and the valve leaflet by pulling tensioning strands of the suture extending from the anchor body out of the heart while preventing forces applied on the length of the suture extending between the anchor body and the valve leaflet due to movement of the leaflet from adjusting the length of the suture extending between the anchor body and the valve leaflet, wherein the means for retaining a suture within the anchor body is a pair of apertures extending through opposing sides of the anchor body and a sleeve disposed around the opposing sides of the anchor body.

10. The anchor of claim 9, wherein the suture is configured to be retained by extending out of one of the apertures at the opposing sides of the anchor body and being wrapped around the sleeve.

11. The anchor of claim 9, wherein the pair of apertures includes a proximal aperture extending through the opposing sides of the anchor body and a distal aperture extending through the opposing sides of the anchor body.

12. The anchor of claim 11, wherein the distal aperture is generally circular at the opposing sides of the anchor body and the proximal apertures are generally elongate at the opposing sides of the anchor body.

13. The anchor of claim 11, wherein the sleeve is positioned around the proximal aperture at the opposing sides of the anchor body.

14. The anchor of claim 13, wherein the suture is configured to be retained by extending into the anchor body, out of the distal aperture at the opposing sides of the anchor body, and wrapping around the sleeve through the proximal aperture at the opposing sides of the anchor body.

15. An anchor configured to be implanted into a heart wall of a heart of a patient to anchor a suture extending from a valve leaflet of the heart as an artificial chordae, the anchor comprising:
    an anchor body; and
    means for retaining a suture within the anchor body, wherein the means for retaining the suture is configured to enable adjustment of a length of the suture extending between the anchor body and the valve leaflet by pulling tensioning strands of the suture extending from the anchor body out of the heart while preventing forces applied on the length of the suture extending between the anchor body and the valve leaflet due to movement of the leaflet from adjusting the length of the suture extending between the anchor body and the valve leaflet, wherein the means for retaining a suture within the anchor body is a pair of pins disposed within the anchor body, the pair of pins comprising a generally cylindrical first bar extending across an entire width of the anchor body and a generally cylindrical second bar extending across the entire width of the anchor body.

16. The anchor of claim 15, wherein the pair of pins are oriented in a generally horizontal configuration with respect to each other.

17. The anchor of claim 15, wherein the pair of pins are oriented in a generally vertical configuration with respect to each other.

18. The anchor of claim 15, further comprising means for adjusting a clamping force by which the pins retain the suture.

19. The anchor of claim 18, wherein the means for adjusting a clamping force comprises a leaf spring that biases the pins into a compressed configuration to retain the suture by a clamping force between the pins.

20. The anchor of claim 19, wherein the leaf spring is configured to be engaged to separate the pins to lessen the clamping force on the suture.

21. The anchor of claim 18, wherein the means for adjusting a clamping force comprises a sleeve extending around the anchor body.

22. The anchor of claim 21, wherein the sleeve is configured to be actuated to separate the pins to lessen the clamping force on the suture.

* * * * *